US008962227B2

(12) United States Patent
Tanaka et al.

(10) Patent No.: US 8,962,227 B2
(45) Date of Patent: *Feb. 24, 2015

(54) ELECTROPHOTOGRAPHIC PHOTOSENSITIVE MEMBER, PROCESS CARTRIDGE, ELECTROPHOTOGRAPHIC APPARATUS, METHOD OF PRODUCING ELECTROPHOTOGRAPHIC PHOTOSENSITIVE MEMBER, AND UREA COMPOUND

(75) Inventors: Masato Tanaka, Tagata-gun (JP); Masaki Nonaka, Suntou-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 96 days.

This patent is subject to a terminal disclaimer.

(21) Appl. No.: 13/477,410

(22) Filed: May 22, 2012

(65) Prior Publication Data
US 2012/0301177 A1 Nov. 29, 2012

(30) Foreign Application Priority Data

May 24, 2011 (JP) ................................. 2011-115863
Apr. 26, 2012 (JP) ................................. 2012-100964

(51) Int. Cl.
*G03G 5/147* (2006.01)
*G03G 5/05* (2006.01)
*C07C 275/28* (2006.01)
*C07C 275/32* (2006.01)
*C07C 275/40* (2006.01)
*C07D 309/12* (2006.01)
*G03G 5/07* (2006.01)

(52) U.S. Cl.
CPC ............ *G03G 5/0503* (2013.01); *C07C 275/28* (2013.01); *C07C 275/32* (2013.01); *C07C 275/40* (2013.01); *C07D 309/12* (2013.01); *G03G 5/0589* (2013.01); *G03G 5/071* (2013.01); *G03G 5/14734* (2013.01); *G03G 5/14786* (2013.01); *G03G 5/14791* (2013.01)
USPC ......... 430/66; 430/58.35; 430/58.7; 430/130; 430/132; 430/133

(58) Field of Classification Search
USPC ............... 430/58.35, 58.7, 66, 130, 132, 133; 399/159
See application file for complete search history.

(56) References Cited

U.S. PATENT DOCUMENTS

| 4,444,863 | A | 4/1984 | Sano | |
|---|---|---|---|---|
| 5,035,969 | A | 7/1991 | Kondo | |
| 6,080,518 | A | 6/2000 | Levin et al. | |
| 8,557,488 | B2 * | 10/2013 | Nagasaka et al. | 430/66 |
| 8,735,032 | B2 * | 5/2014 | Nonaka et al. | 430/66 |
| 2006/0019185 | A1 | 1/2006 | Amamiya et al. | |
| 2006/0110668 | A1 | 5/2006 | Kawasaki et al. | |
| 2011/0129768 | A1 * | 6/2011 | Nonaka et al. | 430/56 |
| 2011/0159419 | A1 | 6/2011 | Iwamoto et al. | |
| 2011/0207041 | A1 | 8/2011 | Miyamoto et al. | |
| 2012/0301178 | A1 | 11/2012 | Nonaka et al. | |
| 2013/0137020 | A1 | 5/2013 | Nagasaka et al. | |
| 2013/0137024 | A1 | 5/2013 | Nonaka et al. | |

FOREIGN PATENT DOCUMENTS

| CN | 1043575 | A | 7/1990 |
|---|---|---|---|
| CN | 001358282 | A | 7/2002 |
| CN | 1410836 | A | 4/2003 |
| CN | 1722004 | A | 1/2006 |
| CN | 001811605 | A | 8/2006 |
| EP | 1198735 | B1 | 2/2007 |
| EP | 2219080 | A2 | 8/2010 |
| EP | 2328032 | A2 | 6/2011 |

(Continued)

OTHER PUBLICATIONS

Diamond, A.S., ed., Handbook of Imaging Materials, Marcel Dekker, Inc., NY (1991), pp. 395-396.*

(Continued)

*Primary Examiner* — Janis L Dote
(74) *Attorney, Agent, or Firm* — Canon U.S.A., Inc. IP Division

(57) ABSTRACT

An electrophotographic photosensitive member that includes the outermost surface layer formed by curing a mixture of a charge transporting substance having a chain-polymerizable functional group and a urea compound represented by the following formula (1) or (2), and a process cartridge and an electrophotographic apparatus each including the electrophotographic photosensitive member.

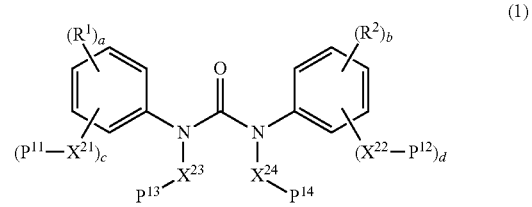

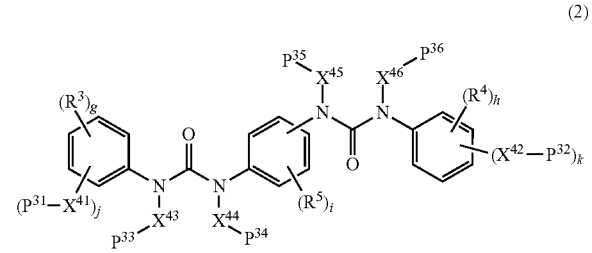

11 Claims, 2 Drawing Sheets

(56) References Cited

FOREIGN PATENT DOCUMENTS

| | | | |
|---|---|---|---|
| JP | 63-097959 | A | 4/1988 |
| JP | 2-230254 | A | 9/1990 |
| JP | 03063657 | A | 3/1991 |
| JP | 08-123055 | A | 5/1996 |
| JP | 2000-066425 | A | 3/2000 |
| JP | 2000-206715 | A | 7/2000 |
| JP | 2000-206716 | A | 7/2000 |
| JP | 2005062302 | A | 3/2005 |
| JP | 2005115353 | A | 4/2005 |
| JP | 2006010816 | A | 1/2006 |
| JP | 2006047949 | A | 2/2006 |
| JP | 2007-279678 | A | 10/2007 |
| JP | 2009015306 | A | 1/2009 |
| JP | 2010085832 | A | 4/2010 |
| JP | 2010156835 | A | 7/2010 |
| JP | 2011137953 | A | 7/2011 |
| JP | 2011-175188 | A | 9/2011 |
| WO | 2005/114331 | A1 | 12/2005 |

OTHER PUBLICATIONS

U.S. Appl. No. 13/477,492, filed May 22, 2012, Hideaki Nagasaka.
U.S. Appl. No. 13/477,561, filed May 22, 2012, Hideaki Nagasaka.
U.S. Appl. No. 13/477,821, filed May 22, 2012, Masaki Nonaka.
U.S. Appl. No. 13/477,876, filed May 22, 2012, Masaki Nonaka.
Sharp Technical Journal No. 101, Aug. 2010, Fukushaki gazo furyo no teiryotekina hyoka hoho no kakuritsu (Establishment of quantitative evaluation method of image defects in copying machine).
Frederick D. Lewis, Todd L. Kurth and Weizhong Liu, "Luminescence of extended and folded N,N'-diarylureas", Photochem,Photobiol,Sci.,2002,1,p. 30-37.
Robert A. Batey, V. Santhakumar, Chiaki Yoshina-Ishii, Scott D. Taylor, "An Efficient New Protocol for the Formation of Unsymmetrical Tri- and Tetrasubstituted Ureas" ,Tetrahedron Letter 39(1998) p. 6267-6270.
Kin-ya Akiba, Satoru Matsunami, Chikahiko Eguchi, and Naoki Inamoto, "Chemistry of Nitrosoimines. VI. Attempted Syntheses of Some Resonance Stabilized Nitrosoimines and Their UV Spectra", Bulletin of the Chemical Society of Japan,vol. 47(4),1974, p. 935-937.
Ernst Bergmann and A. Weitzmann, "The Structure of Urea and Its Derivatives" Transaction of the Faraday Society,34,1938,p. 783-786.

* cited by examiner

ELECTROPHOTOGRAPHIC PHOTOSENSITIVE MEMBER, PROCESS CARTRIDGE, ELECTROPHOTOGRAPHIC APPARATUS, METHOD OF PRODUCING ELECTROPHOTOGRAPHIC PHOTOSENSITIVE MEMBER, AND UREA COMPOUND

BACKGROUND OF THE INVENTION

1. Field of the Invention

The present invention relates to an electrophotographic photosensitive member, a method of producing the electrophotographic photosensitive member, and a process cartridge and an electrophotographic apparatus each including the electrophotographic photosensitive member. The present invention also relates to a urea compound.

2. Description of the Related Art

One example of an electrophotographic photosensitive member installed in an electrophotographic apparatus is an organic electrophotographic photosensitive member containing an organic photoconductive substance (charge generating substance) (hereinafter referred to simply as an "electrophotographic photosensitive member"). Electrophotographic photosensitive members have been widely studied. In particular, for the purpose of extending the life of an electrophotographic photosensitive member and improving image quality, attempts are being made to improve the durability of the electrophotographic photosensitive member.

The improvement of the durability of the electrophotographic photosensitive member may be an improvement of mechanical durability, such as resistance to abrasion and scratches, an improvement of electric potential stability during repeated charging and discharging of electricity, or the prevention of image deletion caused by discharge products. There is a demand for an electrophotographic photosensitive member that satisfies both the improvements of mechanical durability and electric potential stability and the prevention of image deletion in order to achieve an electrophotographic photosensitive member having excellent image stability.

Japanese Patent Laid-Open No. 2000-066425 discloses a technique for providing a surface layer with a polymer produced by the polymerization of a charge transporting substance having two or more chain-polymerizable functional groups. This technique can improve the mechanical durability (abrasion resistance) and the electric potential stability of the electrophotographic photosensitive member. However, the electrophotographic photosensitive member having high abrasion resistance described in Japanese Patent Laid-Open No. 2000-066425 tends to have discharge products (ozone and nitrogen oxide) deposited thereon and cause image deletion in a high temperature and high humidity environment.

Image deletion may be reduced by using an electrophotographic photosensitive member that contains an additive agent. Japanese Patent Laid-Open No. 63-097959 proposes the addition of a urea compound to a photosensitive layer to prevent deterioration of an electrophotographic photosensitive member caused by an active gas.

There is another technique for using a chain-polymerizable additive agent to maintain high mechanical durability of a surface layer that contains a polymer (curable resin) produced by the polymerization of a charge transporting substance having a chain-polymerizable functional group. More specifically, various chain-polymerizable siloxane compounds are used to improve cleaning of the surface of an electrophotographic photosensitive member. Japanese Patent Laid-Open No. 2005-115353 proposes a method of adding a reactive silicone compound that has a dimethylsiloxane structure as a repeating unit. Japanese Patent Laid-Open No. 2006-047949 proposes a method of dispersing an acryl-modified polyorganosiloxane having radical reactivity in a radical polymerizable monomer.

However, the present inventors found that the urea compound described in Japanese Patent Laid-Open No. 63-097959 has an insufficient image deletion preventing effect and tends to decrease electric potential stability. The reactive silicone compound described in Japanese Patent Laid-Open No. 2005-115353 tends to cause film defects because of an insufficient affinity between the dimethylsiloxane structure and a charge transporting substance having an aryl group. Although its dimethylsiloxane structure improves cleaning of the surface of an electrophotographic photosensitive member, the acryl-modified polyorganosiloxane described in Japanese Patent Laid-Open No. 2006-047949 insufficiently prevents image deletion and tends to decrease electric potential stability.

SUMMARY OF THE INVENTION

The present invention provides an electrophotographic photosensitive member having a surface layer that contains a polymer produced by the polymerization of a charge transporting substance having a chain-polymerizable functional group. The electrophotographic photosensitive member has excellent mechanical durability and electric potential stability (prevention of potential variation) and reduces image deletion. The present invention also provides a process cartridge and an electrophotographic apparatus each including the electrophotographic photosensitive member. The present invention also provides a method of producing the electrophotographic photosensitive member. The present invention also provides a urea compound that can prevent deterioration caused by active substances, such as ozone, nitrogen oxide (NOx), and nitric acid.

These can be achieved by the present invention.

The present invention relates to an electrophotographic photosensitive member that includes a support and a photosensitive layer provided on the support. The electrophotographic photosensitive member has a surface layer that contains a polymer produced by the polymerization of a composition that contains a charge transporting substance having a chain-polymerizable functional group and a urea compound having a chain-polymerizable functional group. The urea compound is at least one of a compound represented by the following formula (1) and a compound represented by the following formula (2).

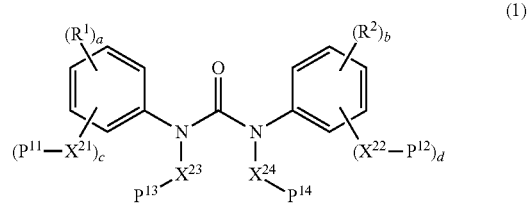

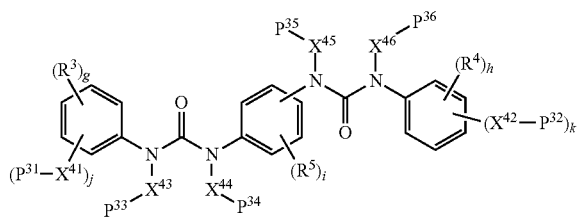

(2)

In the formulas (1) and (2), $R^1$ to $R^5$ each independently represents a substituted or unsubstituted alkyl group, a substituted or unsubstituted alkoxy group, a dialkylamino group, or a halogen atom. $X^{21}$ to $X^{24}$ and $X^{41}$ to $X^{46}$ each independently represents an alkylene group. $P^{11}$ to $P^{14}$ and $P^{31}$ to $P^{36}$ each independently represents a hydrogen atom, an acryloyloxy group, or a methacryloyloxy group, and at least one of $P^{11}$ to $P^{14}$ and at least one of $P^{31}$ to $P^{36}$ each independently represents an acryloyloxy group or a methacryloyloxy group. a, b, g, and h each independently represents an integer number selected from 0 to 5, and i represents an integer number selected from 0 to 4. c, d, j, and k each independently represents 0 or 1.

The present invention also provides a process cartridge detachably attachable to the main body of an electrophotographic apparatus. The process cartridge integrally supports the electrophotographic photosensitive member and at least one device selected from the group consisting of a charging device, a developing device, a transferring device, and a cleaning device.

The present invention also provides an electrophotographic apparatus that includes the electrophotographic photosensitive member, a charging device, an exposure device, a developing device, and a transferring device.

The present invention also provides a method of producing the electrophotographic photosensitive member, which involves forming a coat by the use of a surface-layer coating solution containing the charge transporting substance and the urea compound and forming the surface layer by the polymerization of the charge transporting substance and the urea compound contained in the coat.

The present invention also provides a urea compound represented by the following formula (3) or (4).

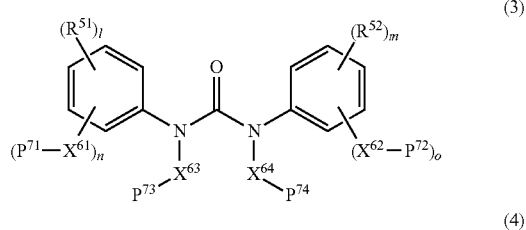

(3)

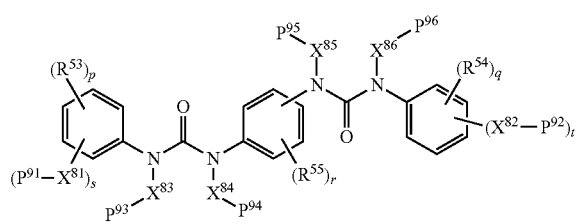

(4)

In the formulas (3) and (4), $R^{51}$ to $R^{55}$ each independently represents an alkyl group, an alkoxy-substituted alkyl group, a halogen-substituted alkyl group, an alkoxy group, an alkoxy-substituted alkoxy group, a halogen-substituted alkoxy group, a dialkylamino group, or a halogen atom. $X^{61}$ to $X^{64}$ and $X^{81}$ to $X^{86}$ each independently represents an alkylene group. $P^{71}$ to $P^{74}$ and $P^{91}$ to $P^{96}$ each independently represents a hydrogen atom, an acryloyloxy group, or a methacryloyloxy group, and at least one of $P^{71}$ to $P^{74}$ and at least one of $P^{91}$ to $P^{96}$ each independently represents an acryloyloxy group or a methacryloyloxy group. l, m, p, and q each independently represents an integer number selected from 0 to 5, r represents an integer number selected from 0 to 4, and n, o, s, and t each independently represents 0 or 1.

The present invention can provide an electrophotographic photosensitive member having a surface layer that contains a polymer produced by the polymerization of a charge transporting substance having a chain-polymerizable functional group. The electrophotographic photosensitive member has excellent electric potential stability and reduces image deletion. The present invention can also provide a process cartridge and an electrophotographic apparatus each including the electrophotographic photosensitive member. The present invention can also provide a method of producing the electrophotographic photosensitive member. The present invention can also provide a urea compound that can prevent deterioration caused by active substances, such as ozone, nitrogen oxide (NOx), and nitric acid.

Further features of the present invention will become apparent from the following description of exemplary embodiments with reference to the attached drawings.

DESCRIPTION OF THE EMBODIMENTS

Figure 1:
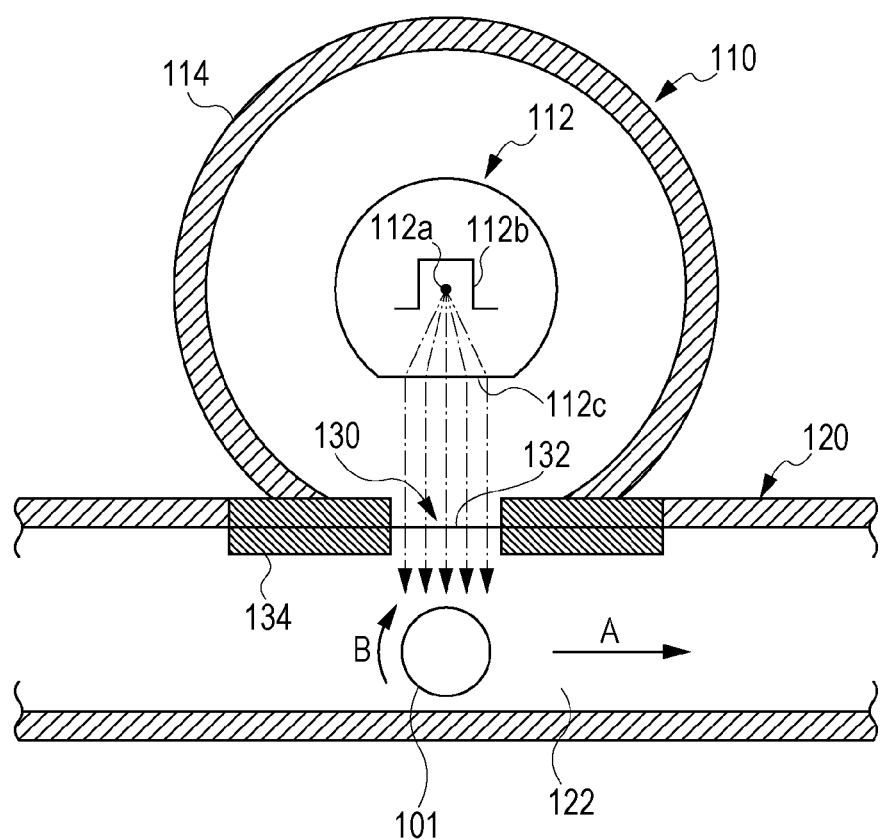
FIG. 1 is a schematic view of an electron-beam irradiation apparatus for use in the production of an electrophotographic photosensitive member according to an embodiment of the present invention.

As described above, an electrophotographic photosensitive member according to an embodiment of the present invention includes a support (electroconductive support) and a photosensitive layer provided on the support. The electrophotographic photosensitive member has a surface layer that contains a polymer (curable resin) produced by the polymerization of a composition that contains a charge transporting substance having a chain-polymerizable functional group and a urea compound having a chain-polymerizable functional group. The urea compound is at least one of a compound represented by the following formula (1) and a compound represented by the following formula (2).

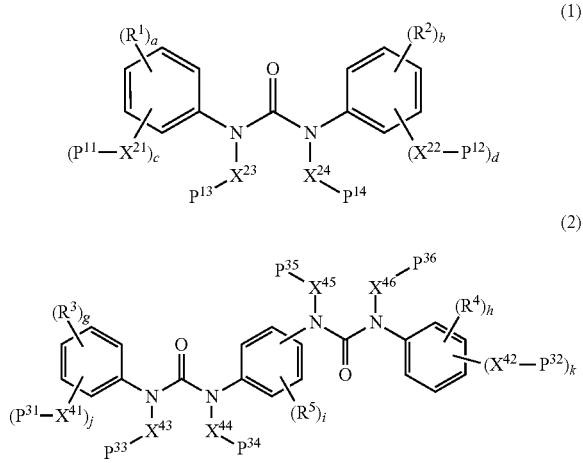

In the formulas (1) and (2), $R^1$ to $R^5$ each independently represents a substituted or unsubstituted alkyl group, a substituted or unsubstituted alkoxy group, a dialkylamino group, or a halogen atom. $X^{21}$ to $X^{24}$ and $X^{41}$ to $X^{46}$ each independently represents an alkylene group. $P^{11}$ to $P^{14}$ and $P^{31}$ to $P^{36}$ each independently represents a hydrogen atom, an acryloyloxy group, or a methacryloyloxy group, and at least one of $P^{11}$ to $P^{14}$ and at least one of $P^{31}$ to $P^{36}$ each independently represents an acryloyloxy group or a methacryloyloxy group. a, b, g, and h each independently represents an integer number selected from 0 to 5, i represents an integer number selected from 0 to 4, and c, d, j, and k each independently represents 0 or 1.

An electrophotographic photosensitive member according to the present invention has excellent mechanical durability and electric potential stability and reduces image deletion. The present inventors believe the reason for this as follows.

A technical literature indicates that discharge products (ozone and nitrogen oxide) deposited on the surface of an electrophotographic photosensitive member react with water in a humid environment to produce nitric acid and causes image deletion (Sharp Technical Journal No. 101, August, 2010, "Fukushakigazofuryo no teiryotekinahyokahoho no kakuritsu (Establishment of quantitative evaluation method of image defects in copying machine)"). Nitric acid deposited on the surface layer of the electrophotographic photosensitive member acts on a charge transporting substance in the electrophotographic photosensitive member to produce an ion pair having a relatively long life, which changes the surface resistivity of the surface layer. This can result in an insufficient light area potential at a boundary between an image-forming portion and a non-image-forming portion and consequently a low optical density of the image-forming portion (a blurred image or no image), which is called image deletion.

A urea compound according to an embodiment of the present invention has an aryl group adjacent to its urea moiety and an alkylene group or an alkyl group on the nitrogen atoms. The aryl group adjacent to the urea moiety rather than an aryl group of a charge transporting substance preferentially forms an ion pair having a relatively short life with nitric acid derived from discharge products. This can reduce variations in the surface resistivity of the surface layer and provide a sufficient light area potential at a boundary between an image-forming portion and a non-image-forming portion. This will prevent a decrease in the optical density of the image-forming portion and reduce image deletion.

A urea compound according to an embodiment of the present invention having the structure described above (the structure having an aryl group adjacent to the urea moiety and an alkylene group or an alkyl group on the nitrogen atoms) does not significantly inhibit polymerization (chain polymerization). Thus, an acryloyloxy group or a methacryloyloxy group of a urea compound according to an embodiment of the present invention can be efficiently copolymerized with a charge transporting substance having a chain-polymerizable functional group to form a polymer having a high degree of polymerization.

Because of such characteristics, an electrophotographic photosensitive member produced with a urea compound according to an embodiment of the present invention can have excellent mechanical durability and electric potential stability and reduce image deletion.

An electrophotographic photosensitive member according to an embodiment of the present invention includes a support and a photosensitive layer provided on the support.

The photosensitive layer may be a monolayer photosensitive layer that contains a charge generating substance and a charge transporting substance or a multilayer (function-separated) photosensitive layer that includes a charge generating layer containing a charge generating substance and a charge transporting layer containing a charge transporting substance. An electrophotographic photosensitive member according to an embodiment of the present invention can have a multilayer photosensitive layer. The charge transporting layer may also have a multilayer structure. The charge transporting layer may be covered with a protective layer.

Thus, a surface layer of an electrophotographic photosensitive member according to an embodiment of the present invention may be a charge transporting layer or a protective layer.

A surface layer of an electrophotographic photosensitive member according to an embodiment of the present invention contains a polymer produced by the polymerization of a composition that contains a charge transporting substance having a chain-polymerizable functional group and a urea compound having a chain-polymerizable functional group. The urea compound is at least one of a compound represented by the formula (1) and a compound represented by the formula (2).

The polymer is produced by the polymerization of the chain-polymerizable functional group of the charge transporting substance and the chain-polymerizable functional group (an acryloyloxy group or a methacryloyloxy group) of the urea compound.

Examples of the substituted or unsubstituted alkyl group in the formulas (1) and (2) include, but are not limited to, unsubstituted alkyl groups, such as a methyl group, an ethyl group, a propyl group, and a butyl group, alkoxy-substituted alkyl groups, such as a methoxymethyl group and an ethoxymethyl group, and halogen-substituted alkyl groups, such as a trifluoromethyl group and a trichloromethyl group. Examples of the substituted or unsubstituted alkoxy group include, but are not limited to, unsubstituted alkoxy groups, such as a methoxy group, an ethoxy group, and a propoxy group, alkoxy-substituted alkoxy groups, such as a methoxymethoxy group and an ethoxymethoxy group, and halogen-substituted alkoxy groups, such as a trifluoromethoxy group and a trichloromethoxy group. Examples of the dialkylamino group include, but are not limited to, a dimethylamino group and a diethylamino group. Examples of the alkylene group include, but are not limited to, a methylene group, an ethylene group, a propylene group, and a butylene group.

a, b, g, h, and i in the formulas (1) and (2) of a urea compound according to an embodiment of the present invention can be 0.

c, d, j, and k in the formulas (1) and (2) of a urea compound according to an embodiment of the present invention can be 0.

When at least one of $X^{21}$ to $X^{24}$ and $X^{41}$ to $X^{46}$ in the formulas (1) and (2) of a urea compound according to an embodiment of the present invention is an ethylene group or a n-propylene group, the polymerization reaction can be promoted.

The following are specific examples of a compound represented by the formula (1) and a compound represented by the formula (2). The present invention is not limited to these examples.

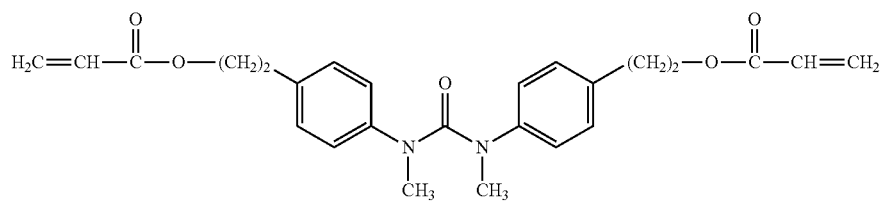
(1-1)

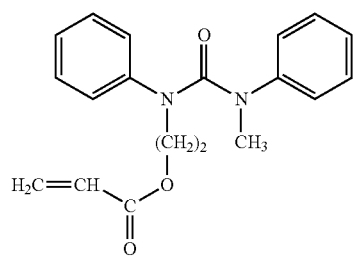
(1-2)

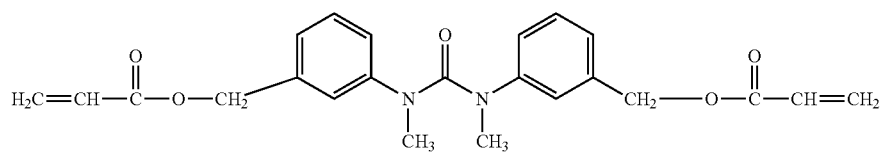
(1-3)

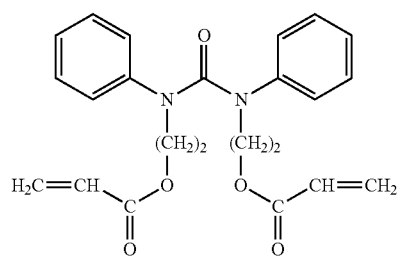
(1-4)

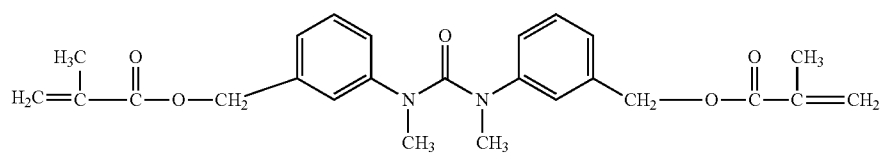
(1-5)

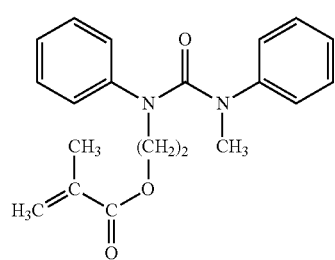
(1-6)

-continued
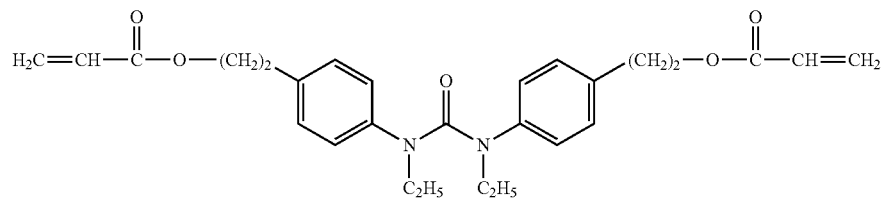
(1-7)
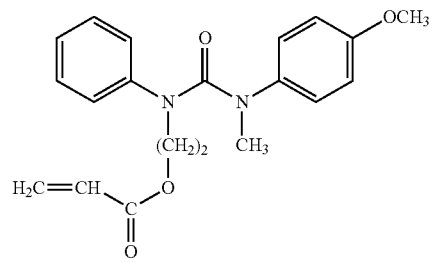
(1-8)
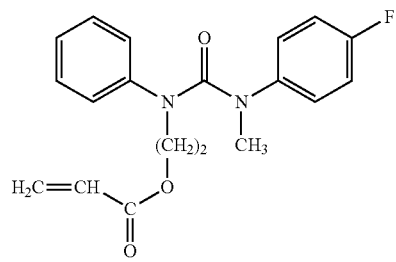
(1-9)
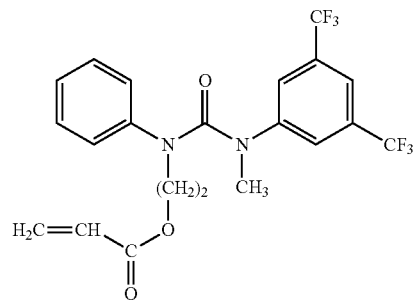
(1-10)
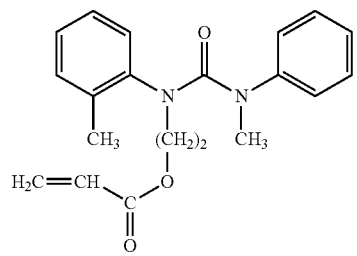
(1-11)
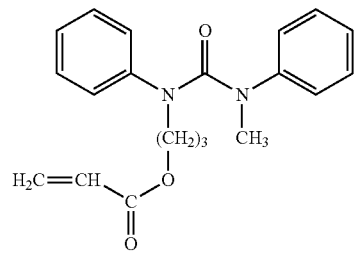
(1-12)
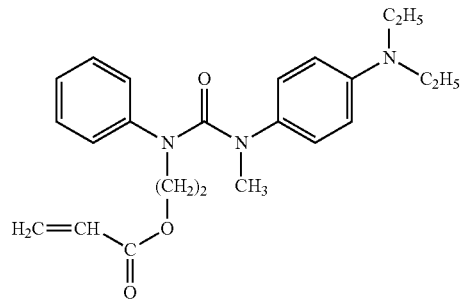
(1-13)
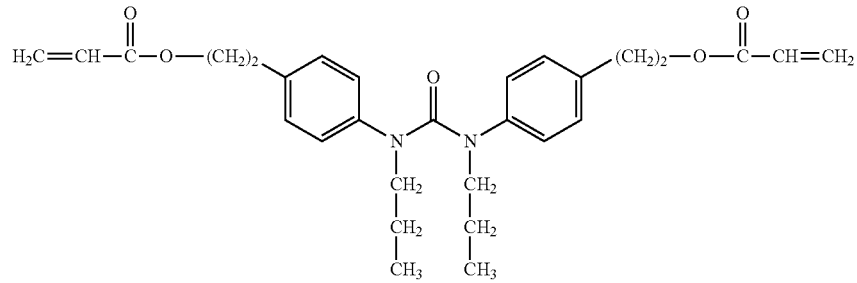
(1-14)
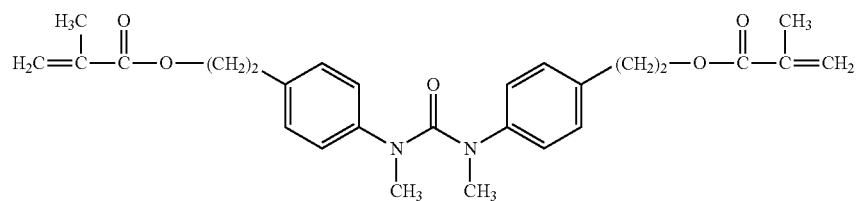
(1-15)

-continued
(2-1)
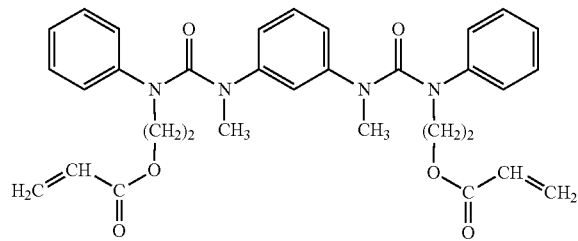
(2-2)
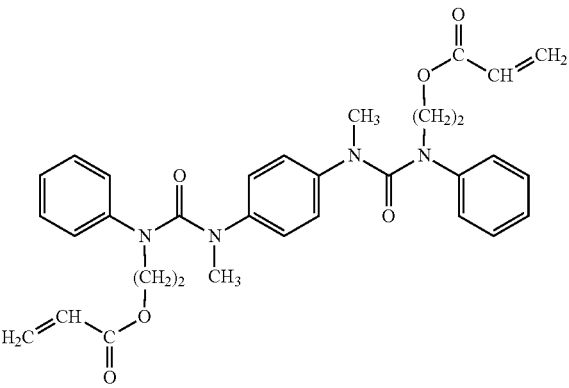
(2-3)
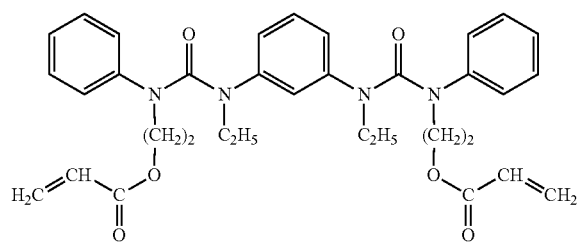
(2-4)
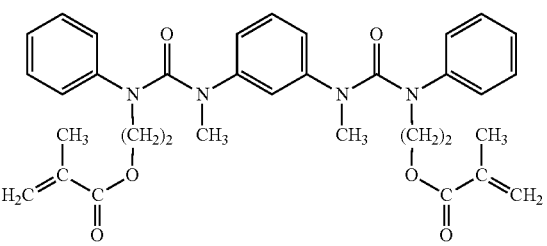
(2-5)
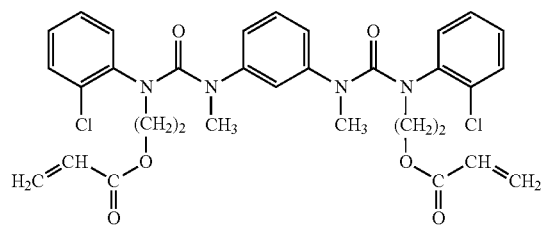
(2-6)
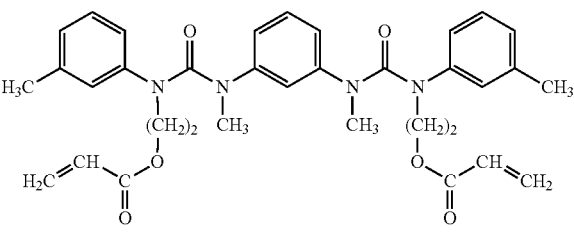
(2-7)
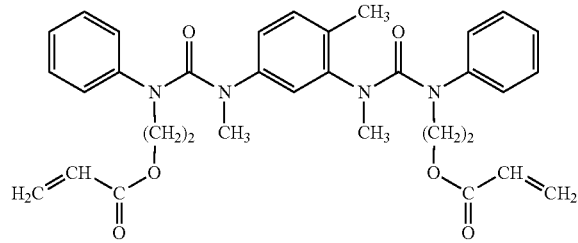
(2-8)
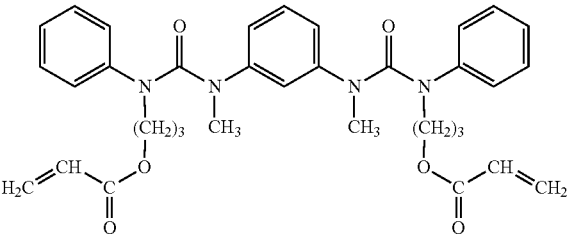
(2-9)
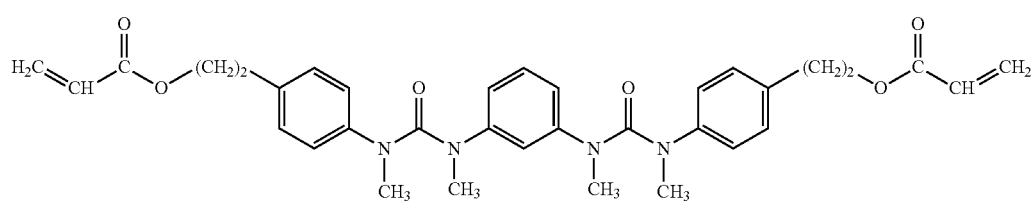
(2-10)
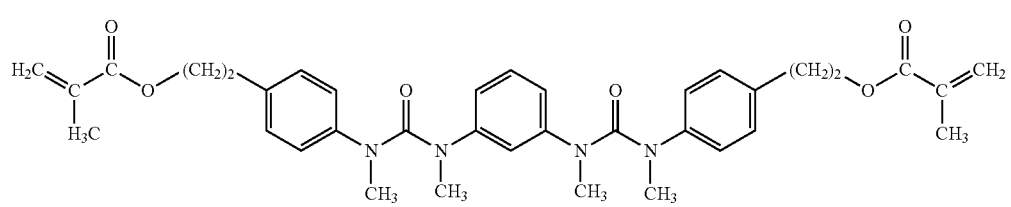

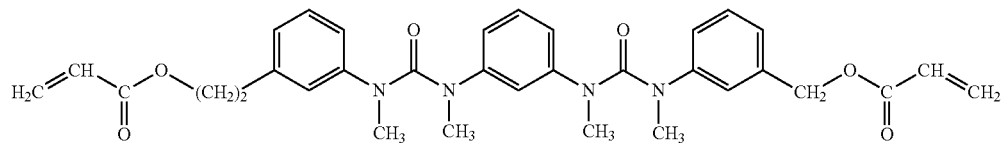
(2-11)

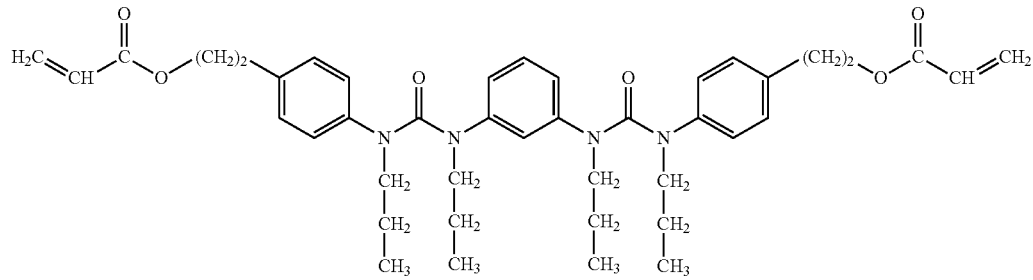
(2-12)

Among these exemplary compounds, in the present invention, compounds represented by the formulas (1-1), (1-3), (1-5), (1-15), (2-1), (2-4), (2-8), (2-9), (2-10), and (2-11) may be used.

The urea compound can be synthesized by esterification of a urea compound having a hydroxy group with an acrylating agent, such as an acryloyl chloride or a methacryloyl chloride.

The urea compound having a hydroxy group can be produced by performing a condensation reaction between an aniline derivative having a hydroxy group and urea to form a urea derivative having a hydroxy group, protecting the hydroxy group of the urea derivative with a tetrahydropyranyl ether, performing N-alkylation of NH of the urea position, and deprotecting the urea derivative. The urea compound having a hydroxy group can also be produced by protecting a hydroxy group of a urea compound produced by an addition reaction between an aniline derivative having a hydroxy group and a phenyl isocyanate derivative or a phenylene diisocyanate derivative in the same manner as described above, performing N-alkylation of NH of the urea position, and deprotecting the urea compound.

The amount of urea compound in a surface layer according to an embodiment of the present invention is preferably 1% by mass or more and 60% by mass or less, more preferably 5% by mass or more and 40% by mass or less, of the total solid mass of the surface-layer coating solution. Satisfying these ranges results in an excellent image deletion preventing effect and high electric potential stability.

In an electrophotographic photosensitive member according to an embodiment of the present invention, the mechanical durability can be improved when a charge transporting substance having a chain-polymerizable functional group and a urea compound having a chain-polymerizable functional group have three or more chain-polymerizable functional groups (acryloyloxy group(s) and/or methacryloyloxy group(s)) in total.

Polymerization of the charge transporting substance and the urea compound having such structures can form a cubic network structure (three-dimensional network structure). Such a network structure imparts sufficient mechanical durability to the surface layer.

The surface layer contains a charge transporting substance having a chain-polymerizable functional group.

The term "polymerization (chain polymerization)", as used herein, refers to unsaturated polymerization, ring-opening polymerization, or isomerization polymerization, in which a polymerization reaction proceeds via a radical or ionic intermediate. The term "chain-polymerizable functional group", as used herein, refers to a functional group that is available in such a polymerization reaction. Japanese Patent Laid-Open No. 2006-010816 discloses specific examples of such a chain-polymerizable functional group. A chain-polymerizable functional group for use in the present invention may be an acryloyloxy group or a methacryloyloxy group. A urea compound having an acryloyloxy group or a methacryloyloxy group has a good affinity.

A satisfactory three-dimensional network structure can be formed when the charge transporting substance having a chain-polymerizable functional group has two or more chain-polymerizable functional groups per molecule. In the case that the charge transporting substance can be used in combination with a polyfunctional monomer (a compound having two or more chain-polymerizable functional groups per molecule and no charge transporting ability) to increase mechanical strength, the charge transporting substance may have only one chain-polymerizable functional group per molecule.

The charge transporting substance having a chain-polymerizable functional group is a compound that has charge transporting ability. The charge transporting substance generally has an aryl group or a heteroaryl group. Examples of the charge transporting substance include, but are not limited to, oxazole derivatives, oxadiazole derivatives, imidazole derivatives, triarylamine derivatives, 9-(p-diethylaminostyryl)anthracene, 1,1-bis-(4-dibenzylaminophenyl)propane, styrylanthracene, styrylpyrazoline, phenylhydrazones, thiazole derivatives, triazole derivatives, phenazine derivatives, acridine derivatives, benzofuran derivatives, benzimidazole derivatives, thiophene derivatives, and N-phenylcarbazole derivatives.

A charge transporting substance having a chain-polymerizable functional group for use in the present invention can be found in Japanese Patent Laid-Open Nos. 2000-066425, 2000-206715, and 2000-206716. Use of a compound represented by the following formula (5) can result in high mechanical durability and electric potential stability.

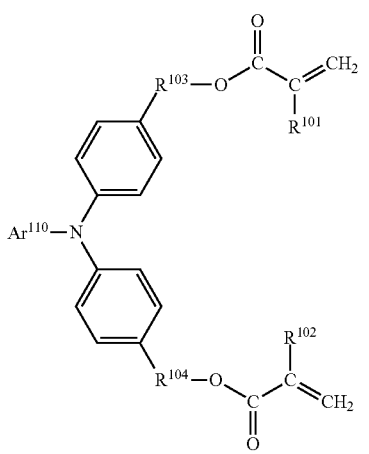

(5)

In the formula (5), $Ar^{110}$ represents an alkyl group, and/or an aryl group optionally having an alkoxy group. $R^{101}$ and $R^{102}$ each independently represents a hydrogen atom or a methyl group. $R^{103}$ and $R^{104}$ each independently represents an alkylene group having 1 to 4 carbon atoms. Examples of the aryl group include, but are not limited to, a phenyl group, a biphenylyl group, and a fluorenyl group. Examples of the alkyl group include, but are not limited to, a methyl group, an ethyl group, a propyl group, and a butyl group. Examples of the alkoxy group include, but are not limited to, a methoxy group and an ethoxy group.

The amount of charge transporting substance having a chain-polymerizable functional group may be 40% by mass or more and 95% by mass or less of the total solid mass of the surface-layer coating solution. Satisfying this range results in sufficient electric potential stability.

A surface layer of an electrophotographic photosensitive member according to an embodiment of the present invention may contain various additive agents. Examples of the additive agents include, but are not limited to, antidegradants, such as antioxidants and ultraviolet absorbers, lubricants, such as polytetrafluoroethylene (PTFE) resin fine particles and fluorocarbons, and polymerization control agents, such as polymerization initiators and polymerization terminators.

In an electrophotographic photosensitive member according to an embodiment of the present invention, the surface layer is formed on the charge transporting layer when the protective layer is the surface layer and on the charge generating layer when the charge transporting layer is the surface layer. The surface layer may be formed by forming a coat by the use of a surface-layer coating solution that contains a charge transporting substance having a chain-polymerizable functional group and a urea compound having a chain-polymerizable functional group dissolved in a solvent and polymerizing the charge transporting substance and the urea compound contained in the coat.

Examples of the solvent of the surface-layer coating solution include, but are not limited to, alcohol solvents, such as methanol, ethanol, and propanol, ketone solvents, such as acetone, methyl ethyl ketone, and cyclohexanone, ester solvents, such as ethyl acetate and butyl acetate, ether solvents, such as tetrahydrofuran and dioxane, halogen solvents, such as 1,1,2,2,3,3,4-heptafluorocyclopentane, dichloromethane, dichloroethane, and chlorobenzene, aromatic solvents, such as benzene, toluene, and xylene, and cellosolve solvents, such as methyl cellosolve and ethyl cellosolve. These solvents may be used alone or in combination.

The structure of an electrophotographic photosensitive member according to an embodiment of the present invention will be described below.

Support

A support of an electrophotographic photosensitive member according to an embodiment of the present invention may be electroconductive (an electroconductive support). For example, the support is made of a metal or alloy, such as aluminum, copper, chromium, nickel, zinc, or stainless steel. The support may be a polyester or polycarbonate insulative substrate covered with a thin film made of a metal, such as aluminum or copper, or an electroconductive material, such as indium oxide or tin oxide. The support may contain electroconductive particles, such as carbon black, tin oxide particles, or titanium oxide particles, dispersed in a resin. The support may also be a plastic containing an electroconductive binder resin. The support may be cylindrical or a sheet. In order to prevent the occurrence of interference fringes, the support may have a rough surface. More specifically, the support may be subjected to cutting, surface roughening, or alumite treatment.

In an electrophotographic photosensitive member according to an embodiment of the present invention, an electroconductive layer containing electroconductive particles and a resin may be formed on the support. The electroconductive layer may be formed by applying an electroconductive-layer coating solution containing electroconductive particles and a resin to the support and drying the coating solution. The electroconductive layer contains a powder including the electroconductive particles. Examples of the electroconductive particles include, but are not limited to, carbon black, acetylene black, powders of metals, such as aluminum, zinc, copper, chromium, nickel, and silver, alloy powders, and powders of metal oxides, such as tin oxide and indium-tin oxide (ITO).

Examples of the resin for use in the electroconductive layer include, but are not limited to, acrylic resin, alkyd resin, epoxy resin, phenolic resin, butyral resin, polyacetal resin, polyurethane, polyester, polycarbonate, and melamine resin.

Examples of the solvent for use in the electroconductive-layer coating solution include, but are not limited to, ether solvents, alcohol solvents, ketone solvents, and aromatic hydrocarbon solvents. The thickness of the electroconductive layer is preferably 0.2 μm or more and 40 μm or less, more preferably 5 μm or more and 40 μm or less.

An electrophotographic photosensitive member according to an embodiment of the present invention may include an intermediate layer between the support or the electroconductive layer and the photosensitive layer (the charge generating layer). The intermediate layer may be formed by applying an intermediate-layer coating solution containing a resin to the support or the electroconductive layer and drying or hardening the coating solution.

Examples of the resin for use in the intermediate layer include, but are not limited to, poly(vinyl alcohol) resin, poly-N-vinylimidazole resin, poly(ethylene oxide) resin, ethylcellulose, an ethylene-acrylic acid copolymer, casein, polyamide resin, N-methoxymethylated 6 nylon, copolymerized nylon, glue, and gelatin. The intermediate layer may contain the electroconductive particles described above. The thickness of the intermediate layer is preferably 0.05 μm or more and 40 μm or less, more preferably 0.4 μm or more and 20 μm or less. The intermediate layer may contain semiconductive particles, an electron transporting substance, or an electron accepting substance.

Photosensitive Layer

An electrophotographic photosensitive member according to an embodiment of the present invention includes a photosensitive layer (a charge generating layer and a charge transporting layer) on the support, the electroconductive layer, or the intermediate layer.

Examples of the charge generating substance for use in an electrophotographic photosensitive member according to an embodiment of the present invention include, but are not limited to, pyrylium, thiapyrylium dyes, phthalocyanine compounds, anthanthrone pigments, dibenzpyrenequinone pigments, pyranthrone pigments, azo pigments, indigo pigments, quinacridone pigments, and quinocyanine pigments.

The charge generating layer may be formed by applying a charge generating layer coating solution and drying the coating solution. The charge generating layer coating solution is prepared by dispersing a charge generating substance together with a binder resin and a solvent. The charge generating layer may also be an evaporated film of a charge generating substance.

Examples of the binder resin for use in a charge generating layer of a multilayer photosensitive layer according to an embodiment of the present invention include, but are not limited to, polymers and copolymers of vinyl compounds, such as styrene, vinyl acetate, and vinyl chloride, poly(vinyl alcohol) resin, poly(vinyl acetal) resin, poly(vinyl benzal) resin, polycarbonate resin, polyester resin, polysulfone resin, poly(phenylene oxide), polyurethane resin, cellulose resin, phenolic resin, melamine resin, silicon resin, and epoxy resin. These may be used alone or in combination as a mixture or a copolymer.

In the charge generating layer, the ratio of the binder resin to the charge generating substance may be 0.3 or more and 2 or less based on mass. The dispersion may be performed with a homogenizer, ultrasonic waves, a ball mill, a sand mill, an attritor, or a rolling mill. The thickness of the charge generating layer is preferably 0.01 µm or more and 5 µm or less, more preferably 0.1 µm or more and 1 µm or less. The charge generating layer may contain an intensifier, an antioxidant, an ultraviolet absorber, and/or a plasticizer, if necessary.

In the case that a charge transporting layer of a multilayer photosensitive layer is the surface layer, the charge transporting layer contains a polymer produced by the polymerization of a composition that contains a charge transporting substance having a chain-polymerizable functional group and a urea compound having a chain-polymerizable functional group. The charge transporting substance having a chain-polymerizable functional group and the urea compound are described above. In the case that a protective layer formed on a charge transporting layer is the surface layer, the charge transporting layer may be formed by applying a charge transporting layer coating solution that contains a charge transporting substance and a binder resin to the charge generating layer and drying the coating solution.

In this case, examples of the charge transporting substance include, but are not limited to, pyrazoline compounds, oxazole compounds, triarylalkane compounds, triarylamine compounds, carbazole compounds, stilbene compounds, and hydrazone compounds.

The binder resin for use in the charge transporting layer is the same as the resin for use in the charge generating layer, for example, a polyester resin, a polycarbonate resin, a polyarylate resin, a polysulfone resin, or a polystyrene resin. In the case that the surface layer is the protective layer, the ratio of the charge transporting substance to the charge transporting layer is preferably 30% by mass or more and 70% by mass or less, more preferably 40% by mass or more and 60% by mass or less.

The thickness of the charge transporting layer is preferably in the range of 1 to 50 µm, more preferably 10 to 30 µm.

In the case that the surface layer is the protective layer, as described above, the protective layer contains a polymer produced by the polymerization of a composition that contains a charge transporting substance having a chain-polymerizable functional group and a urea compound having a chain-polymerizable functional group.

In the case that the surface layer is the charge transporting layer or the protective layer, the surface layer may contain a charge transporting substance as well as the polymer. The mechanical durability and the electric potential stability of the electrophotographic photosensitive member can be improved when the charge transporting substance constitutes 10% by mass or less of the total mass of the surface layer.

These coating solution may be applied by dip coating, spray coating, bead coating, blade coating, beam coating, or spinner coating.

In the case of a monolayer photosensitive layer, a surface layer according to an embodiment of the present invention may be formed on the monolayer photosensitive layer containing a charge generating substance and a charge transporting substance disposed on the support.

In order to improve cleaning of the surface of an electrophotographic photosensitive member, a surface layer of the electrophotographic photosensitive member may be subjected to surface roughening. The surface roughening may be performed by a method of rubbing the outermost surface layer with a polishing sheet or a method of transferring asperities of a mold to the surface layer.

The charge transporting substance having a chain-polymerizable functional group and the urea compound may be polymerizable utilizing heat, light (such as ultraviolet rays), or radioactive rays (such as an electron ray). If necessary, a polymerization initiator may be used in the polymerization. In particular, polymerization utilizing radioactive rays, such as an electron ray, does not necessarily use a polymerization initiator.

Polymerization utilizing an electron ray can produce a three-dimensional network structure having a very high density and achieve excellent electric potential stability. Because of short and efficient polymerization, polymerization utilizing an electron ray has high productivity. In addition, because the transmission of an electron ray can be easily controlled, polymerization is not significantly inhibited even in a thick film or even when a shielding substance, such as an additive agent, is present in the surface layer. However, with a certain type of chain-polymerizable functional group or central skeleton, polymerization proceeds negligibly. In such a case, a polymerization initiator may be used within the bounds of not affecting the polymerization. An accelerator of an electron ray may be of a scanning type, an electrocurtain type, a broad beam type, a pulse type, or a laminar type.

The following are the conditions for electron ray irradiation. In embodiments of the present invention, the accelerating voltage is preferably 120 kV or less, more preferably 80 kV or less. The electron ray absorbed dose is preferably in the range of $1 \times 10^3$ to $1 \times 10^5$ Gy, more preferably $5 \times 10^3$ to $5 \times 10^4$ Gy. With an absorbed dose of $1 \times 10^3$ Gy or more and $1 \times 10^5$ Gy or less, the electrophotographic photosensitive member can have excellent mechanical durability and electric potential stability.

FIG. 1 is a schematic view of an electron-beam irradiation apparatus for use in the production of an electrophotographic photosensitive member according to an embodiment of the present invention. The electron-beam irradiation apparatus in the present embodiment includes an electron ray generator 110, an irradiation chamber 120, and an irradiation window 130.

The electron ray generator 110 includes a terminal 112 for generating an electron ray and an accelerator tube 114 for accelerating the electron ray generated by the terminal 112 in a vacuum space (acceleration space). The interior of the electron ray generator 110 is maintained at a pressure in the range of $10^{-4}$ to $10^{-6}$ Pa with a diffusion pump (not shown). The terminal 112 includes a linear filament 112a for emitting thermoelectrons, a housing 112b for supporting the filament 112a, and a grid 112c for controlling the thermoelectrons emitted by the filament 112a.

The electron ray generator 110 includes a heating power supply (not shown) for heating the filament 112a to generate thermoelectrons, a control direct-current power source (not shown) for applying a voltage between the filament 112a and the grid 112c, and an accelerating direct-current power source (not shown) for applying a voltage between the grid 112c and a window foil 132 disposed in the irradiation window 130.

The irradiation chamber 120 includes an irradiation space 122 in which the surface of a cylindrical target (an electrophotographic photosensitive member) 101 is irradiated with an electron ray. In order to prevent oxygen from inhibiting the polymerization of a surface layer of an electrophotographic photosensitive member, the interior of the irradiation chamber 120 has an inert gas atmosphere. Examples of the inert gas include, but are not limited to, nitrogen, argon, and helium. The cylindrical target 101 is transported in the irradiation chamber 120 in the direction of arrow A, for example, with a conveyer. While the cylindrical target 101 is irradiated with an electron ray through the irradiation window 130, the cylindrical target 101 is rotated in the direction of arrow B.

The irradiation window 130 includes the window foil 132 made of metallic foil and a window frame structure 134 for cooling and supporting the window foil 132. An electron ray enters the irradiation chamber 120 through the window foil 132. An electric current from the heating power supply passes through and heats the filament 112a, allowing the filament 112a to emit thermoelectrons. Thermoelectrons passing through the grid 112c are effectively extracted as an electron ray. The electron ray passing through the grid 112c is accelerated in the acceleration space in the accelerator tube 114 by an accelerating voltage applied between the grid 112c and the window foil 132 with the accelerating direct-current power source. The electron ray passes through the window foil 132 and reaches the cylindrical target 101 under the irradiation window 130 in the irradiation chamber 120. In general, the beam current can be controlled by setting the heating power supply and the accelerating direct-current power source at predetermined values and adjusting the control direct-current power source. In accordance with an embodiment of the present invention, the electron ray irradiation in the inert gas atmosphere may be followed by heating in an inert gas atmosphere.

An electrophotographic apparatus according to an embodiment of the present invention will be described below.

Figure 2:
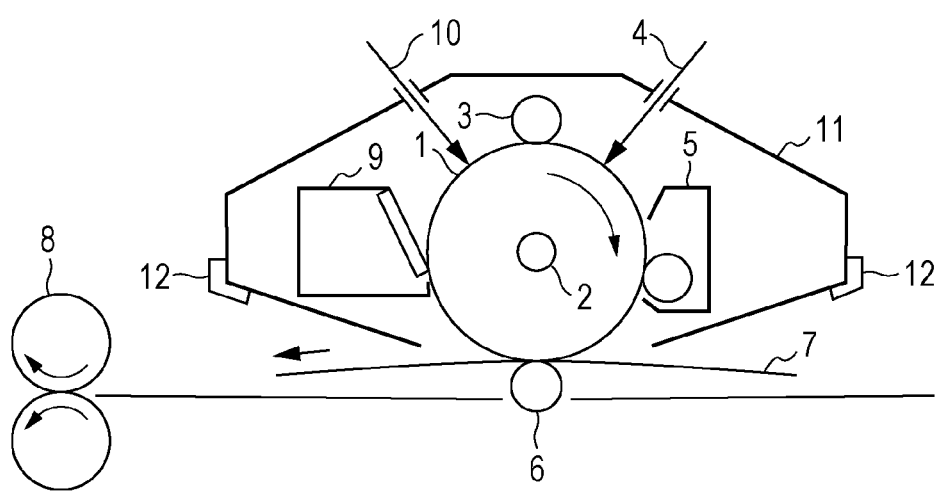
FIG. 2 is a schematic view of an electrophotographic apparatus that includes a process cartridge including an electrophotographic photosensitive member according to an embodiment of the present invention.

FIG. 2 illustrates an electrophotographic apparatus that includes a process cartridge including an electrophotographic photosensitive member according to an embodiment of the present invention.

In FIG. 2, a drum-type electrophotographic photosensitive member 1 according to an embodiment of the present invention is rotated around a shaft 2 in the direction of the arrow at a predetermined peripheral speed (process speed). During the rotation, the surface of the electrophotographic photosensitive member 1 is uniformly positively or negatively charged at a predetermined potential by a charging device (primary charging device) 3. The electrophotographic photosensitive member 1 is then irradiated with intensity-modulated exposure light 4 emitted from an exposure device (not shown), such as a slit exposure device or a laser beam scanning exposure device, in response to the time-series electric digital image signals of intended image information. In this way, electrostatic latent images corresponding to the intended image information are successively formed on the surface of the electrophotographic photosensitive member 1.

The electrostatic latent images are then subjected to normal or reversal development with a toner in a developing device 5 to be made visible as toner images. The toner images on the electrophotographic photosensitive member 1 are successively transferred to a transferring member 7 by a transferring device 6. The transferring member 7 taken from a paper feeder (not shown) in synchronism with the rotation of the electrophotographic photosensitive member 1 is fed between the electrophotographic photosensitive member 1 and the transferring device 6. A bias voltage having polarity opposite to the polarity of the electric charges of the toner is applied to the transferring device 6 with a bias power supply (not shown). The transferring device may be an intermediate transfer device that includes a primary transfer member, an intermediate transfer member, and a secondary transfer member.

The transferring member 7 is then separated from the electrophotographic photosensitive member and is transported to a fixing device 8. After the toner images are fixed, the transferring member 7 is output from the electrophotographic apparatus as an image-formed article (such as a print or a copy).

Deposits, such as residual toner, on the surface of the electrophotographic photosensitive member 1 after the toner images have been transferred are removed with a cleaning device 9. The residual toner may be recovered with the developing device 5. After the electricity is removed with pre-exposure light 10 from a pre-exposure device (not shown), the electrophotographic photosensitive member 1 is again used for image forming. In the case that the charging device 3 is a contact charging device, such as a charging roller, pre-exposure is not necessarily required.

A plurality of components selected from the electrophotographic photosensitive member 1, the charging device 3, the developing device 5, the transferring device 6, and the cleaning device 9 may be housed in a container to provide a process cartridge. The process cartridge may be detachably attached to the main body of an electrophotographic apparatus, such as a copying machine or a laser-beam printer. For example, at least one device selected from the group consisting of the charging device 3, the developing device 5, the transferring device 6, and the cleaning device 9 may be integrally supported together with the electrophotographic photosensitive member 1 to provide a process cartridge 11, which is detachably attachable to the main body of an electrophotographic apparatus through a guide unit 12, such as rails.

In accordance with an embodiment of the present invention, a urea compound that can prevent deterioration caused by active substances, such as ozone, nitrogen oxide (NOx), and nitric acid, is represented by the following formula (3) or (4).

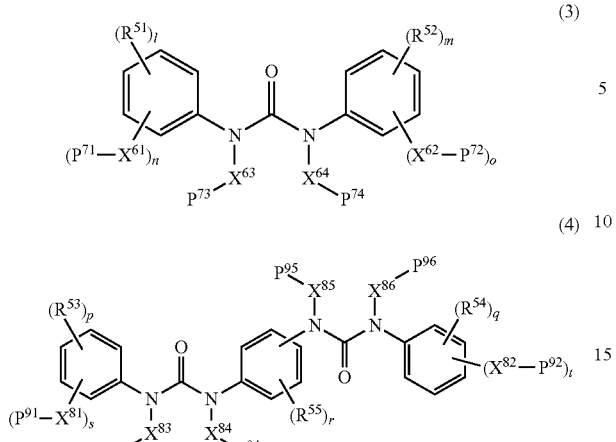

In the formulas (3) and (4), $R^{51}$ to $R^{55}$ each independently represents an alkyl group, an alkoxy-substituted alkyl group, a halogen-substituted alkyl group, an alkoxy group, an alkoxy-substituted alkoxy group, a halogen-substituted alkoxy group, a dialkylamino group, or a halogen atom. $X^{61}$ to $X^{64}$ and $X^{81}$ to $X^{86}$ each independently represents an alkylene group. $P^{71}$ to $P^{74}$ and $P^{91}$ to $P^{96}$ each independently represents a hydrogen atom, an acryloyloxy group, or a methacryloyloxy group, and at least one of $P^{71}$ to $P^{74}$ and at least one of $P^{91}$ to $P^{96}$ each independently represents an acryloyloxy group or a methacryloyloxy group. l, m, p, and q each independently represents an integer number selected from 0 to 5, r represents an integer number selected from 0 to 4, and n, o, s, and t each independently represents 0 or 1.

l, m, p, q, and r in the formulas (3) and (4) of a urea compound according to an embodiment of the present invention can be 0.

n, o, s, and t in the formulas (3) and (4) of a urea compound according to an embodiment of the present invention can be 0.

At least one of $X^{61}$ to $X^{64}$ and $X^{81}$ to $X^{86}$ in the formulas (3) and (4) of a urea compound according to an embodiment of the present invention may be an ethylene group or a n-propylene group.

More specifically, a urea compound according to an embodiment of the present invention may be any one of the compounds (1-1) to (1-15) and (2-1) to (2-12).

Production examples of a urea compound according to an embodiment of the present invention will be described below. In the production examples, "%" means "% by mass", and "part" means "part by mass". Mass spectrometry was performed with Trace DSQ-MASS spectrometer (manufactured by Thermo Electron Co., Ltd.). Infrared spectroscopy (IR) measurement was performed with FT/IR-420 (manufactured by JASCO Corp.). A nuclear magnetic resonance (NMR) spectrum was measured with R-90 (manufactured by Hitachi, Ltd.).

Production Example 1

Manufacture of Exemplary Compound (1-1)

A compound represented by the following formula (A) (1,3-bis[4-(2-hydroxy-ethyl)-phenyl]-urea) was synthesized. 506.2 parts of 3 normal aqueous hydrochloric acid was slowly added dropwise to 200.0 parts of 2-(4-aminophenyl)ethanol in a three-neck flask and was then stirred for 30 minutes. 58.4 parts of urea and 220 parts of ion-exchanged water were added to the mixture, which was then refluxed for 10 hours. After cooling, precipitated crystals were collected with a filter. The crystals were dispersed and washed with 1300 parts of ion-exchanged water and were collected with a filter. The crystals were dispersed and washed with 1000 parts of ethanol, were collected with a filter, and were dried at 30° C. under reduced pressure to yield 171.1 parts of the compound represented by the following formula (A) as slight pink crystals. The following are characteristic peaks of the IR spectrum and NMR data of the product.

IR (cm$^{-1}$, KBr): 3378, 3309, 1638, 1554, 1237, 1054, 1017
$^1$H-NMR (ppm, DMSO-d$_6$): δ=
8.39 (s, 2H, NH)
7.25 (d, 4H, J=8.6 Hz)
7.08 (d, 4H, J=8.6 Hz)
4.95 (brs, 2H, OH)
3.55 (t, 4H, J=7.0 Hz)
2.63 (t, 4H, J=7.0 Hz).

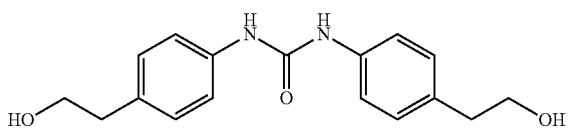

(A)

A compound represented by the following formula (B) (1,3-bis{4-[2-tetrahydro-pyran-2-yloxy]-ethyl}-phenyl}-urea) was synthesized from the compound represented by the formula (A). 149.5 parts of the compound represented by the formula (A) was dissolved in 1500 parts of N,N-dimethylformamide in a three-neck flask. 1.9 parts of p-toluenesulfonic acid monohydrate was added to the solution, which was then cooled to 15° C. 168 parts of 3,4-dihydro-2H-pyran was slowly added dropwise to the solution, which was then stirred for two hours at a temperature in the range of 80° C. to 85° C. After cooling, 2000 parts of water was added to the solution, and extraction was performed with 1000 parts of ethyl acetate twice. The two extracts were combined, were dispersed and washed with 500 parts of water, and were separated. After dispersed and washed with 500 parts of saturated aqueous sodium chloride, the resulting separated organic layer was dried over magnesium sulfate, and the solvent was evaporated under reduced pressure. The residue was passed through an alumina column (solvent: a mixture of toluene and tetrahydrofuran), and the solvent was evaporated under reduced pressure. The resulting crystals were dispersed and washed with 80% aqueous methanol at a temperature in the range of 50° C. to 60° C., were collected with a filter, and were dried at 30° C. under reduced pressure to yield 201.6 parts of the compound represented by the following formula (B) as cream crystals. The following are characteristic peaks of the IR spectrum and NMR data of the product.

IR (cm$^{-1}$, KBr): 3390, 2948, 1710, 1595, 1538, 1514, 1115
$^1$H-NMR (ppm, CDCl$_3$): δ=
7.24 (d, 4H, J=8.6 Hz)
7.11 (d, 4H, J=8.6 Hz)
6.91 (s, 2H, NH)
4.60 (brs, 2H)
4.0-3.4 (m, 8H)
2.83 (t, 4H, J=6.9 Hz)
1.7-1.4 (m, 12H).

(B)

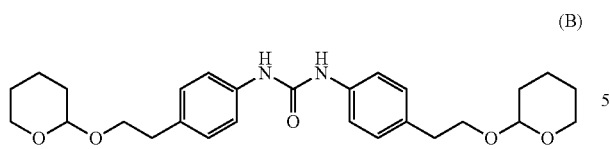

A compound represented by the following formula (C) (1,3-bis[4-(2-hydroxy-ethyl)-phenyl]-1,3-dimethyl-urea) was synthesized from the compound represented by the formula (B). 29.8 parts of 60% sodium hydride and 800 parts of dry N,N-dimethylformamide in a nitrogen atmosphere in a three-neck flask were cooled with ice water. A solution of 159.0 parts of the compound represented by the formula (B) dissolved in 800 parts of dry N,N-dimethylformamide was added dropwise while the solution temperature was controlled in the range of 4° C. to 7° C. After stirring for 30 minutes, 144.5 parts of methyl iodide was added dropwise while the solution temperature was controlled in the range of 4° C. to 11° C. After cooling was stopped, the product was stirred at room temperature for 1.5 hours. 2500 parts of water was added to the product, and extraction was performed with 1000 parts of ethyl acetate three times. The three extracts were combined and were washed with 500 parts of water twice. The resulting organic layer was dried over magnesium sulfate, and the solvent was evaporated under reduced pressure. 1000 parts of methanol and 200 parts of tetrahydrofuran and then 12.8 parts of p-toluenesulfonic acid monohydrate were added to the residue and were stirred at room temperature for five hours. 1000 parts of water was added to the product, and extraction was performed with 2000 parts of ethyl acetate. The extract was dispersed and washed with 300 parts of 5% aqueous sodium hydrogen carbonate, was separated, was dispersed and washed with 500 parts of saturated aqueous sodium chloride, and was separated. The resulting separated organic layer was dried over magnesium sulfate, and the solvent was evaporated under reduced pressure. The residue was purified with a silica gel column (solvent: a mixture of toluene and tetrahydrofuran), and the solvent was evaporated under reduced pressure. The resulting crystals were dispersed and washed with n-heptane, were collected with a filter, and were dried at 30° C. under reduced pressure to yield 51.6 parts of the compound represented by the following formula (C) as pale cream crystals. The following are mass spectrometry measurements, characteristic peaks of an IR spectrum, and NMR data.

MS (Direct Prove): 328.14

Calculated Exact Mass: 328.18

IR (cm$^{-1}$, KBr): 3406, 2868, 1622, 1599, 1514, 1376, 1055, 568

$^1$H-NMR (ppm, CDCl$_3$): δ=

6.89 (d, 4H, J=8.6 Hz)

6.71 (d, 4H, J=8.6 Hz)

3.74 (t, 4H, J=6.3 Hz)

3.19 (s, 6H, N-Me)

2.70 (t, 4H, J=6.3 Hz)

2.09 (s, 2H, OH).

(C)

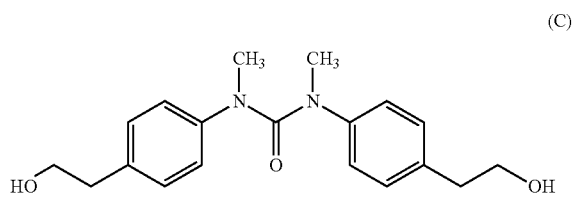 [SMILES: CN(C(=O)N(C)c1ccc(CCO)cc1)c1ccc(CCO)cc1]

The exemplary compound (1-1) was synthesized from the compound represented by the formula (C). 48.6 parts of triethylamine was added to 41.5 parts of the compound represented by the formula (C) and 800 parts of dry tetrahydrofuran in a three-neck flask, which was then cooled with ice water. 34.3 parts of acryloyl chloride was slowly added dropwise while the solution temperature was controlled in the range of 3° C. to 12° C. After cooling was stopped, the product was stirred at room temperature for two hours. 400 parts of 10% aqueous sodium hydroxide was added to the product. After stirring, extraction was performed with 400 parts of ethyl acetate twice. The two extracts were combined and were dispersed and washed with 400 parts of saturated aqueous sodium chloride. The resulting separated organic layer was dried over magnesium sulfate, and the solvent was evaporated under reduced pressure. The residue was dissolved in 500 parts of toluene. Two parts of activated carbon was added to the solution. After stirring at room temperature for 30 minutes, the solution was filtered. The solvent of the filtrate was evaporated under reduced pressure. The residue was purified with a silica gel column (solvent: a mixture of toluene and ethyl acetate), and the solvent was evaporated under reduced pressure to yield 44.6 parts of the exemplary compound (1-1) as a yellow viscous liquid. The following are mass spectrometry measurements, characteristic peaks of an IR spectrum, and NMR data.

MS (Direct Prove): 436.26

Calculated Exact Mass: 436.20

IR (cm$^{-1}$, Neat): 2956, 1724, 1656, 1516, 1356, 1189, 987, 811

$^1$H-NMR (ppm, CDCl$_3$): δ=

6.89 (d, 4H, J=8.6 Hz)

6.71 (d, 4H, J=8.6 Hz)

6.6-5.7 (m, 6H)

4.24 (t, 4H, J=7.0 Hz)

3.15 (s, 6H, N-Me)

2.82 (t, 4H, J=7.0 Hz).

Production Example 2

Production of Exemplary Compound (1-2)

A compound represented by the following formula (D) (1-(2-hydroxyethyl)-3-methyl-1,3-diphenylurea) was synthesized. A solution of 4.8 parts of phenylisocyanate dissolved in 20 parts of tetrahydrofuran was slowly added dropwise to 5.5 parts of N-(2-hydroxyethyl)aniline and 20 parts of tetrahydrofuran in a three-neck flask while stirring. The solution was stirred at room temperature for two hours and was refluxed for one hour. The solvent was evaporated under reduced pressure, and volatile components were evaporated at 80° C. at a reduced pressure of 500 Pa to yield 10.4 parts of cream crystals. 4.3 parts of the cream crystals were dissolved in 40 parts of dry tetrahydrofuran in a three-neck flask. 0.03 parts of p-toluenesulfonic acid monohydrate was added to the solution, to which 2.1 parts of 3,4-dihydro-2H-pyran was then slowly added dropwise. The solution was then stirred at 60° C. for three hours. After cooling, 100 parts of water was added to the solution, and extraction was performed with 50 parts of ethyl acetate three times. The three extracts were combined and were dispersed and washed with 80 parts of saturated aqueous sodium chloride. The resulting separated organic layer was dried over magnesium sulfate, and the solvent was evaporated under reduced pressure to yield 5.6 parts of a brown viscous liquid.

0.7 parts of 60% sodium hydride and 10 parts of dry N,N-dimethylformamide in a nitrogen atmosphere in a three-neck flask were cooled with ice water. A solution of 5.5 parts of the brown viscous liquid dissolved in 15 parts of dry N,N-dimethylformamide was added dropwise while the solution temperature was controlled in the range of 2° C. to 7° C. After stirring for 30 minutes, 3.4 parts of methyl iodide was added dropwise while the solution temperature was controlled in the range of 3° C. to 11° C. After cooling was stopped, the product was stirred at room temperature for 1.5 hours. 50 parts of water was added to the product, and extraction was performed with 30 parts of ethyl acetate three times. The three extracts were combined and were washed with 50 parts of water twice, and the resulting organic layer was dried over magnesium sulfate. The solvent was evaporated under reduced pressure to yield 5.4 parts of an orange viscous liquid. 25 parts of methanol and 0.19 parts of p-toluenesulfonic acid monohydrate were added to 5.3 parts of the orange viscous liquid and were refluxed for three hours. 100 parts of water was added to the product, and extraction was performed with 100 parts of ethyl acetate. The extract was dispersed and washed with 20 parts of 5% aqueous sodium hydrogen carbonate and was separated. After dispersed and washed with 20 parts of saturated aqueous sodium chloride, the resulting separated organic layer was dried over magnesium sulfate, and the solvent was evaporated under reduced pressure. The residue was purified with a silica gel column (solvent: a mixture of toluene and ethyl acetate), and the solvent was evaporated under reduced pressure. The resulting crystals were dispersed and washed with n-heptane, were collected with a filter, and were dried at 30° C. under reduced pressure to yield 2.6 parts of the compound represented by the following formula (D) as white crystals. The following are characteristic peaks of the IR spectrum and NMR data of the product.

IR ($cm^{-1}$, KBr): 3438, 2942, 1626, 1497, 1350, 1029, 754, 694
$^1$H-NMR (ppm, $CDCl_3$): δ=
7.1-6.9 (m, 6H)
6.8-6.6 (m, 4H)
4.41 (t, 1H, J=4.1 Hz, OH)
3.9-3.6 (m, 4H)
3.19 (s, 3H, N-Me).

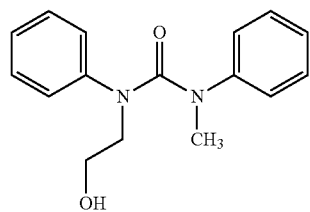

(D)

The exemplary compound (1-2) was synthesized from the compound represented by the formula (D). A three-neck flask was charged with 2.5 parts of the compound represented by the formula (D) and 25 parts of dry tetrahydrofuran. 1.4 parts of triethylamine was added to the mixture, which was then cooled with ice water. 1.0 part of acryloyl chloride was slowly added dropwise while the solution temperature was controlled in the range of 3° C. to 15° C. After cooling was stopped, the product was stirred at room temperature for two hours. 25 parts of 10% aqueous sodium hydroxide was added to the product. After stirring, extraction was performed with 80 parts of ethyl acetate twice. The two extracts were combined and were dispersed and washed with 40 parts of saturated aqueous sodium chloride. The resulting separated organic layer was dried over magnesium sulfate, and the solvent was evaporated under reduced pressure. The residue was purified with a silica gel column (solvent: a mixture of toluene and ethyl acetate), and the solvent was evaporated under reduced pressure to yield 2.6 parts of the exemplary compound (1-2) as a light yellow liquid. The following are mass spectrometry measurements, characteristic peaks of an IR spectrum, and NMR data.

MS (Direct Prove): 324.12
Calculated Exact Mass: 324.15
IR ($cm^{-1}$, Neat): 2954, 1725, 1658, 1652, 1596, 1496, 1188, 754, 694
$^1$H-NMR (ppm, $CDCl_3$): δ=
7.0-6.8 (m, 6H)
6.8-6.6 (m, 4H)
6.3-6.0 (m, 2H)
5.9-5.7 (m, 1H)
4.41 (t, 2H, J=5.5 Hz)
3.88 (t, 2H, J=5.5 Hz)
3.17 (s, 3H, N-Me).

Production Example 3

Production of Exemplary Compound (1-3)

A compound represented by the following formula (E) (1,3-bis(3-hydroxymethyl-phenyl)-urea) was synthesized. 162 parts of 3 normal aqueous hydrochloric acid was slowly added dropwise to 50.0 parts of 3-aminobenzyl alcohol in a three-neck flask and was then stirred for 30 minutes. 16.3 parts of urea and 65 parts of ion-exchanged water were added to the mixture, which was then refluxed for 10 hours. After cooling, precipitated crystals were collected with a filter. The crystals were dispersed and washed with 400 parts of ion-exchanged water and were collected with a filter. The crystals were dispersed and washed with 400 parts of ethanol, were collected with a filter, and were dried at 30° C. under reduced pressure to yield 33.7 parts of the compound represented by the following formula (E) as white crystals.

The following are NMR data.
$^1$H-NMR (ppm, DMSO-$d_6$): δ=
8.56 (s, 2H, NH)
7.5-6.8 (m, 8H)
5.12 (t, 2H, J=5.8 Hz, OH)
4.46 (d, 4H, J=5.8 Hz).

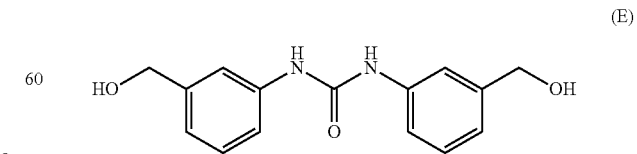

(E)

The compound represented by the following formula (F) (1,3-bis[3-(tetrahydropyran-2-yloxymethyl)-phenyl]-urea) was synthesized from the compound represented by the formula (E). 28.5 parts of the compound represented by the formula (E) was dissolved in 300 parts of N,N-dimethylformamide in a three-neck flask. 0.4 parts of p-toluenesulfonic acid monohydrate was added to the solution, which was then heated to 80° C. 35.2 parts of 3,4-dihydro-2H-pyran was slowly added dropwise to the solution, which was then stirred for five hours at a temperature in the range of 80° C. to 85° C. After cooling, 600 parts of water was added to the solution, and extraction was performed with 500 parts of ethyl acetate twice. The two extracts were combined and were dispersed and washed with 300 parts of water. The resulting separated organic layer was dried over magnesium sulfate, and the solvent was evaporated under reduced pressure. The residue was recrystallized in ethyl acetate, and the resulting crystals were dispersed and washed with hot water at a temperature in the range of 50° C. to 60° C. The crystals were collected with a filter and were dried at 30° C. under reduced pressure to yield 33.8 parts of the compound represented by the following formula (F) as white crystals. The following are characteristic peaks of the IR spectrum and NMR data of the product.

IR (cm$^{-1}$, KBr): 3325, 2952, 1656, 1567, 1034
$^1$H-NMR (ppm, DMSO-d$_6$): δ=
8.63 (s, 2H, NH)
7.5-6.9 (m, 8H)
4.8-4.3 (m, 6H)
4.0-3.3 (m, 4H)
1.7-1.4 (Br, 12H).

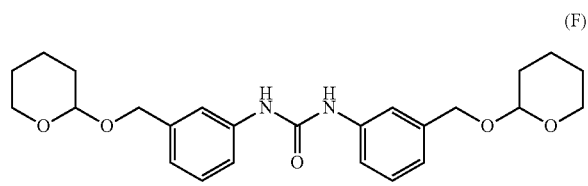 [SMILES: O=C(Nc1cccc(COC2CCCCO2)c1)Nc1cccc(COC2CCCCO2)c1]

(F)

A compound represented by the following formula (G) (1,3-bis(3-hydroxymethyl-phenyl)-1,3-dimethyl-urea) was synthesized from the compound represented by the formula (F). 7.2 parts of 60% sodium hydride and 360 parts of dry N,N-dimethylformamide in a nitrogen atmosphere in a three-neck flask were cooled with ice water. 36.0 parts of the compound represented by the formula (F) was added to the mixture while the solution temperature was controlled in the range of 4° C. to 7° C. The mixture was then stirred at room temperature for 30 minutes. The mixture was then cooled with ice water, and 34.8 parts of methyl iodide was added dropwise while the solution temperature was controlled in the range of 4° C. to 11° C. After cooling was stopped, the product was stirred at room temperature for one hour. 750 parts of water was added to the product, and extraction was performed with 300 parts of ethyl acetate three times. The three extracts were combined and were washed with 200 parts of water twice. The resulting organic layer was dried over magnesium sulfate, and the solvent was evaporated under reduced pressure. 400 parts of ethanol and 2.1 parts of p-toluenesulfonic acid monohydrate were added to the residue and were refluxed for 3.5 hours. The solvent was evaporated under reduced pressure. 900 parts of ethyl acetate and 180 parts of 5% aqueous sodium hydrogen carbonate were added, and extraction was performed. The extract was dispersed and washed with 100 parts of saturated aqueous sodium chloride. The resulting separated organic layer was dried over magnesium sulfate, and the solvent was evaporated under reduced pressure. The residue was purified with a silica gel column (solvent: a mixture of toluene and tetrahydrofuran), and the solvent was evaporated under reduced pressure. The resulting crystals were dispersed and washed with n-heptane, were collected with a filter, and were dried at 30° C. under reduced pressure to yield 19.4 parts of the compound represented by the following formula (G) as white crystals. The following are characteristic peaks of the IR spectrum and NMR data of the product.

IR (cm$^{-1}$, KBr): 3394, 2855, 1666, 1634, 1602, 1439, 1372, 700
$^1$H-NMR (ppm, CDCl$_3$): δ=
7.1-6.6 (m, 8H)
4.43 (d, 4H, CH$_2$—OH)
3.22 (s, 6H, N-Me)
2.60 (brs, 2H, OH).

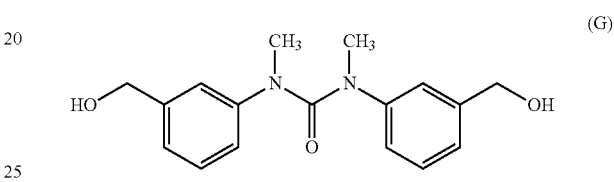

(G)

The exemplary compound (1-3) was synthesized from the compound represented by the formula (G). A three-neck flask was charged with 19.0 parts of the compound represented by the formula (G) and 600 parts of dry tetrahydrofuran. 21.1 parts of triethylamine was added to the mixture, which was then cooled with ice water. 17.2 part of acryloyl chloride was slowly added dropwise while the solution temperature was controlled in the range of 4° C. to 15° C. After cooling was stopped, the product was stirred at room temperature for two hours. 150 parts of 10% aqueous sodium hydroxide was added to the product. After stirring, extraction was performed with 200 parts of ethyl acetate twice. The two extracts were combined and were dispersed and washed with 200 parts of saturated aqueous sodium chloride. The resulting separated organic layer was dried over magnesium sulfate, and the solvent was evaporated under reduced pressure. The residue was dissolved in 200 parts of toluene. One part of activated carbon was added to the solution. After stirring at room temperature for 30 minutes, the solution was filtered. The solvent of the filtrate was evaporated under reduced pressure. The residue was purified with a silica gel column (solvent: a mixture of toluene and ethyl acetate), and the solvent was evaporated under reduced pressure to yield 15.7 parts of the exemplary compound (1-3) as a light yellow viscous liquid. The following are mass spectrometry measurements, characteristic peaks of an IR spectrum, and NMR data.

MS (Direct Prove): 408.03
Calculated Exact Mass: 408.17
IR (cm$^{-1}$, Neat): 2958, 1725, 1659, 1407, 1354, 1187, 698
$^1$H-NMR (ppm, CDCl$_3$): δ=
7.0-6.7 (m, 8H)
6.4-5.8 (m, 6H)
4.98 (s, 4H)
3.20 (s, 6H, N-Me).

Production Example 4

Synthesis of Exemplary Compound (2-1)

A compound represented by the following formula (H) (1-(2-hydroxyethyl)-3-{3-[3-(2-hydroxyethyl)-3-phenylureide]-phenyl}-1-phenylurea) was synthesized. A solution of 5.0 parts of 1,3-phenylene diisocyanate dissolved in 50 parts of tetrahydrofuran was slowly added dropwise to 21.4 parts of N-(2-hydroxyethyl)aniline and 110 parts of tetrahydrofuran in a three-neck flask while stirring. The resulting solution was refluxed for two hours, and the solvent was evaporated under reduced pressure. The residue was purified with a silica gel column (solvent: a mixture of toluene and tetrahydrofuran), and the solvent was evaporated under reduced pressure. The resulting crystals were dispersed and washed with toluene, were collected with a filter, and were dried at 30° C. under reduced pressure to yield 11.7 parts of the compound represented by the following formula (H) as white crystals. The following are mass spectrometry measurements, characteristic peaks of an IR spectrum, and NMR data.

MS (Direct Prove): 434.16
Calculated Exact Mass: 434.20
IR (cm$^{-1}$, KBr): 3432, 3318, 1674, 1642, 1530, 1488, 1420, 1292, 1209, 1051, 700
$^1$H-NMR (ppm, DMSO): δ=
7.84 (s, 2H, NH)
7.41 (t, 3H, J=7.7 Hz)
7.34-7.25 (m, 7H)
7.04-7.00 (m, 3H)
4.90 (t, 2H, J=5.0 Hz, OH)
3.71 (t, 4H, J=6.1 Hz)
3.53 (q, 4H)

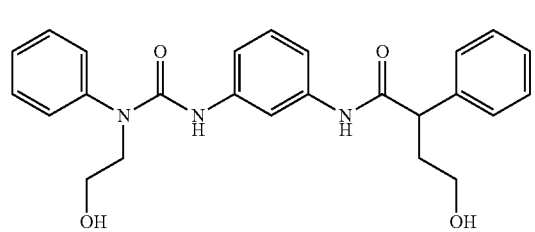

(H)

A compound represented by the following formula (1) (1-(2-hydroxyethyl)-3-{3-[3-(2-hydroxyethyl)-1-methyl-3-phenylureide]-phenyl}-3-methyl-1-phenylurea) was synthesized from the compound represented by the formula (H). A three-neck flask was charged with 10.5 parts of the compound represented by the formula (H), 100 parts of dry tetrahydrofuran, and 0.5 parts of p-toluenesulfonic acid monohydrate. 6.1 parts of 3,4-dihydro-2H-pyran was slowly added dropwise to the mixture, which was then stirred for five hours. 200 parts of water was added to the reaction solution, and extraction was performed with 80 parts of ethyl acetate three times. The three extracts were combined and were dispersed and washed with 40 parts of 5% aqueous sodium hydrogen carbonate, and the resulting separated organic layer was dispersed and washed with 60 parts of saturated aqueous sodium chloride. The separated organic layer was dried over magnesium sulfate, and the solvent was evaporated under reduced pressure to yield 16.0 parts of a yellow viscous liquid.

2.1 parts of 60% sodium hydride and 10 parts of dry N,N-dimethylformamide in a nitrogen atmosphere in a three-neck flask were cooled with ice water. A solution of 16.0 parts of the yellow viscous liquid dissolved in 50 parts of dry N,N-dimethylformamide was added dropwise while the solution temperature was controlled in the range of 2° C. to 12° C. After stirring for 30 minutes, 10.3 parts of methyl iodide was added dropwise while the solution temperature was controlled in the range of 2° C. to 12° C. After cooling was stopped, the product was stirred at room temperature for one hour. 100 parts of water was added to the product, and extraction was performed with 70 parts of ethyl acetate three times. The three extracts were combined and were washed with 50 parts of water twice, and the resulting organic layer was dried over magnesium sulfate. The solvent was evaporated under reduced pressure to yield 16.2 parts of a yellow viscous liquid. 80 parts of ethanol and 0.3 parts of p-toluenesulfonic acid monohydrate were added to 16.2 parts of the yellow viscous liquid and were refluxed for seven hours. 40 parts of 5% aqueous sodium hydrogen carbonate was added to the product, and extraction was performed with 150 parts of ethyl acetate. The extract was dispersed and washed with 40 parts of saturated aqueous sodium chloride. The resulting separated organic layer was dried over magnesium sulfate, and the solvent was evaporated under reduced pressure. The residue was purified with a silica gel column (solvent: a mixture of toluene and tetrahydrofuran), and the solvent was evaporated under reduced pressure. The resulting crystals were dispersed and washed with n-hexane, were collected with a filter, and were dried at 30° C. under reduced pressure to yield 7.4 parts of the compound represented by the following formula (I) as white crystals. The following are mass spectrometry measurements, characteristic peaks of an IR spectrum, and NMR data.

MS (Direct Prove): 462.37
Calculated Exact Mass: 462.23
IR (cm$^{-1}$, KBr): 3408, 2931, 1619, 1593, 1385, 1067, 696
$^1$H-NMR (ppm, DMSO): δ=
7.04-6.19 (m, 14H)
4.67 (br, 2H, OH)
3.51 (brs, 8H)
2.8 (s, 6H, N-Me)

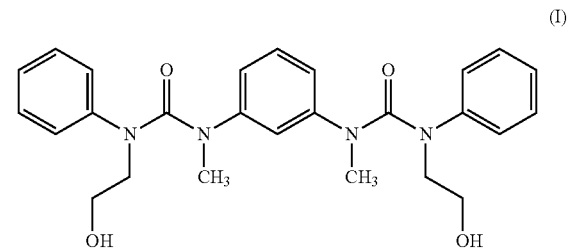 [SMILES: CN(C(=O)N(CCO)c1ccccc1)c1cccc(N(C)C(=O)N(CCO)c2ccccc2)c1]

(I)

The exemplary compound (2-1) was synthesized from the compound represented by the formula (1). A three-neck flask was charged with 6.2 parts of the compound represented by the formula (1) and 120 parts of dry tetrahydrofuran. 6.8 parts of triethylamine was added to the mixture, which was then cooled with ice water. 4.9 parts of acryloyl chloride was slowly added dropwise while the solution temperature was controlled in the range of 3° C. to 11° C. After cooling was stopped, the product was stirred at room temperature for one hour and then at 35° C. for one hour. 100 parts of 1% aqueous sodium hydroxide was added to the product. After stirring, extraction was performed with 100 parts of ethyl acetate twice. The two extracts were combined and were dispersed and washed with 80 parts of saturated aqueous sodium chloride. The resulting separated organic layer was dried over magnesium sulfate, and the solvent was evaporated under reduced pressure. The residue was purified with a silica gel column (solvent: a mixture of toluene and ethyl acetate), and the solvent was evaporated under reduced pressure to yield light yellow crystals. The crystals were recrystallized in a mixed solvent of toluene and hexane to yield 2.8 parts of the exemplary compound (2-1) as white crystals. The following are mass spectrometry measurements, characteristic peaks of an IR spectrum, and NMR data.

MS (Direct Prove): 570.02
Calculated Exact Mass: 570.25
IR (cm$^{-1}$, Neat): 1736, 1652, 1376, 1207, 985, 762, 696
$^1$H-NMR (ppm, CDCl$_3$): δ=
6.99-5.69 (m, 20H)
4.36 (t, 4H, J=5.6 Hz)
3.81 (t, 4H, J=5.6 Hz)
2.91 (s, 6H, N-Me).

Production Example 5

Synthesis of Exemplary Compound (2-4)

The exemplary compound (2-4) was synthesized from the compound represented by the formula (1). A three-neck flask was charged with 1.0 part of the compound represented by the formula (1) and 20 parts of dry tetrahydrofuran. 1.1 parts of triethylamine was added to the mixture, which was then cooled with ice water. 0.9 parts of methacryloyl chloride was slowly added dropwise while the solution temperature was controlled in the range of 1° C. to 5° C. After cooling was stopped, the product was stirred at room temperature for three hours. 10 parts of 10% aqueous sodium hydroxide was added to the product. After stirring, extraction was performed with 30 parts of ethyl acetate twice. The two extracts were combined and were dispersed and washed with 20 parts of saturated aqueous sodium chloride. The resulting separated organic layer was dried over magnesium sulfate, and the solvent was evaporated under reduced pressure. The residue was purified with a silica gel column (solvent: a mixture of n-hexane and ethyl acetate), and the solvent was evaporated under reduced pressure to yield pale yellow crystals. The crystals were recrystallized in a mixed solvent of toluene and n-hexane to yield 0.6 parts of the exemplary compound (2-4) as white crystals. The following are mass spectrometry measurements, characteristic peaks of an IR spectrum, and NMR data.

MS (Direct Prove): 598.32
Calculated Exact Mass: 598.28
IR (cm$^{-1}$, Neat): 2954, 1732, 1719, 1649, 1597, 1367, 1166, 764, 698
$^1$H-NMR (ppm, CDCl$_3$): δ=
6.99-5.89 (m, 16H)
5.49 (t, 4H, J=1.7 Hz)
4.34 (t, 4H, J=5.6 Hz)
3.83 (t, 4H, J=5.6 Hz)
2.90 (s, 6H, N-Me)
1.85 (s, 6H)

Production Example 6

Synthesis of Exemplary Compound (1-15)

The exemplary compound (1-15) was synthesized from the compound represented by the formula (C). 7.7 parts of triethylamine was added to 5.0 parts of the compound represented by the formula (C) and 100 parts of dry tetrahydrofuran in a three-neck flask, which was then cooled with ice water. 6.4 parts of methacryloyl chloride was slowly added dropwise while the solution temperature was controlled in the range of 4° C. to 10° C. After cooling was stopped, the product was stirred at room temperature for four hours. 50 parts of 10% aqueous sodium hydroxide was added to the product. After stirring, extraction was performed with 50 parts of ethyl acetate twice. The two extracts were combined and were dispersed and washed with 60 parts of saturated aqueous sodium chloride. The resulting separated organic layer was dried over magnesium sulfate, and the solvent was evaporated under reduced pressure. The residue was purified with a silica gel column (solvent: a mixture of n-hexane and ethyl acetate), and the solvent was evaporated under reduced pressure to yield pale yellow crystals. The crystals were recrystallized in n-hexane to yield 3.1 parts of the exemplary compound (1-15) as white crystals. The following are mass spectrometry measurements, characteristic peaks of an IR spectrum, and NMR data.

MS (Direct Prove): 464.33
Calculated Exact Mass: 464.23
IR (cm$^{-1}$, Neat): 2960, 1710, 1663, 1517, 1357, 1324, 1160
$^1$H-NMR (ppm, CDCl$_3$): δ=
6.90 (d, 4H, J=8.5 Hz)
6.70 (d, 4H, J=8.5 Hz)
6.09 (Brs, 2H)
5.55 (t, 2H, J=1.5 Hz)
4.22 (t, 4H, J=7.0 Hz)
3.15 (s, 6H, N-Me)
2.82 (t, 4H, J=7.0 Hz)
1.94 (s, 6H).

EXAMPLES

The present invention will be further described in the following examples and comparative examples. The term "part" in the examples means "part by mass". The film thickness in the examples and comparative examples was measured with an eddy-current thickness gauge (trade name: Fischerscope, manufactured by Fischer Instruments K.K.) or was calculated from the mass per unit area by specific gravity conversion.

Example 1

An aluminum cylinder having a diameter of 30 mm, a length of 357.5 mm, and a thickness of 1 mm was used as a support (electroconductive support).

50 parts of titanium oxide particles covered with tin oxide containing 10% antimony oxide (trade name: ECT-62, manufactured by Titan Kogyo, Ltd.), 25 parts of a resole phenolic resin (trade name: Phenolite J-325, manufactured by Dainippon Ink and Chemicals, Inc., solid content 70% by mass), 20 parts of methyl cellosolve, 5 parts of methanol, and 0.002 parts of a silicone oil (a polydimethylsiloxane-polyoxyalkylene copolymer having an average molecular weight of 3000) were dispersed for two hours with a sand mill using glass beads having a diameter of 0.8 mm to prepare an electroconductive-layer coating solution.

The electroconductive-layer coating solution was applied to the support by dip coating and was dried at 140° C. for 30 minutes to form an electroconductive layer having a thickness of 15 μm.

2.5 parts of a nylon 6-66-610-12 quaterpolymer resin (trade name: CM 8000, manufactured by Toray Industries, Inc.) and 7.5 parts of an N-methoxymethylated 6nylon resin (trade name: TORESIN EF-30T, manufactured by Nagase ChemteX Corp.) were dissolved in a mixed solvent of 100 parts of methanol and 90 parts of butanol to prepare an intermediate-layer coating solution.

The intermediate-layer coating solution was applied to the electroconductive layer by dip coating and was dried at 100° C. for 10 minutes to form an intermediate layer having a thickness of 0.7 μm.

11 parts of hydroxy gallium phthalocyanine crystals (a charge generating substance) were prepared. The crystals had strong peaks at Bragg angles (2θ±0.2°) of 7.4° and 28.2° in CuKα characteristic X-ray diffraction. A mixture of 5 parts of a poly(vinyl butyral) resin (trade name: S-LECBX-1, manufactured by Sekisui Chemical Co., Ltd.) and 130 parts of cyclohexanone was dispersed with 500 parts of glass beads having a diameter of 1 mm at 1800 rpm for two hours while the mixture was cooled with cooling water at 18° C. After dispersion, the mixture was diluted with 300 parts of ethyl acetate and 160 parts of cyclohexanone to prepare a charge generating layer coating solution.

The average particle size (median) of the hydroxy gallium phthalocyanine crystals in the charge generating layer coating solution was 0.18 μm as measured with a centrifugal particle size analyzer (trade name: CAPA-700) manufactured by Horiba, Ltd., the principle of which is based on liquid phase sedimentation.

The charge generating layer coating solution was applied to the intermediate layer by dip coating and was dried at 110° C. for 10 minutes to form a charge generating layer having a thickness of 0.17 μm.

5 parts of a compound represented by the following formula (6) (a charge transporting substance), 5 parts of a compound represented by the following formula (7) (a charge transporting substance), and 10 parts of a polycarbonate resin (trade name: LUPILON Z400, manufactured by Mitsubishi Gas Chemical Co., Inc.) were dissolved in a mixed solvent of 70 parts of monochlorobenzene and 30 parts of dimethoxymethane to prepare a charge transporting layer coating solution.

The charge transporting layer coating solution was applied to the charge generating layer by dip coating and was dried at 100° C. for 30 minutes to form a charge transporting layer having a thickness of 18 μm.

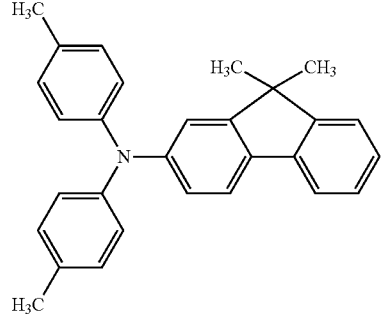

(6)

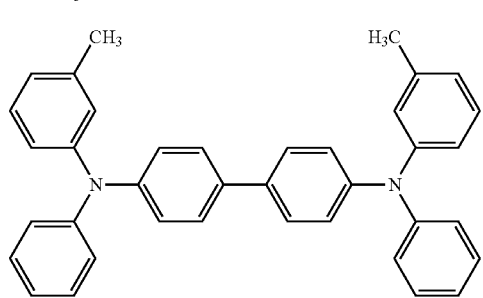

(7)

90 parts of a compound represented by the following formula (8) and 10 parts of the exemplary compound (1-1) were dissolved in 100 parts of n-propanol. 100 parts of 1,1,2,2,3,3,4-heptafluorocyclopentane (trade name: ZEORORA H, manufactured by Zeon Corp.) was added to the solution to prepare a protective layer coating solution.

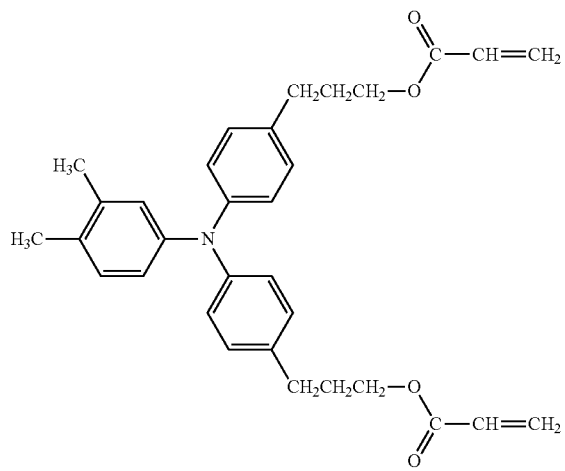

(8)

The protective layer coating solution was applied to the charge transporting layer by dip coating, and the resulting coat was heat-treated at 50° C. for five minutes. The coat was then irradiated with an electron ray for 1.6 seconds in a nitrogen atmosphere at an accelerating voltage of 80 kV and an absorbed dose of 19000 Gy. The coat was then heat-treated at 125° C. for 30 seconds in a nitrogen atmosphere. The processes from the electron ray irradiation to the 30-second heat treatment were performed at an oxygen concentration of 19 ppm. The coat was then heat-treated at 110° C. for 20 minutes in the atmosphere to form a protective layer having a thickness of 5 μm.

In this manner, an electrophotographic photosensitive member was produced. The electrophotographic photosensitive member included the support, the electroconductive layer, the intermediate layer, the charge generating layer, the charge transporting layer, and the protective layer. The protective layer was the surface layer.

Example 2

An electrophotographic photosensitive member was produced in the same manner as in Example 1 except that the protective layer coating solution was prepared using the exemplary compound (1-2) instead of the exemplary compound (1-1).

Example 3

An electrophotographic photosensitive member was produced in the same manner as in Example 1 except that the protective layer coating solution was prepared using the exemplary compound (1-3) instead of the exemplary compound (1-1).

Example 4

An electrophotographic photosensitive member was produced in the same manner as in Example 1 except that the protective layer coating solution was prepared using the exemplary compound (2-1) instead of the exemplary compound (1-1).

Example 5

An electrophotographic photosensitive member was produced in the same manner as in Example 1 except that the protective layer coating solution was prepared using a protective layer coating solution that contained 95 parts of the compound represented by the formula (8) and 5 parts of the exemplary compound (1-1).

Example 6

An electrophotographic photosensitive member was produced in the same manner as in Example 1 except that the protective layer coating solution was prepared using a protective layer coating solution that contained 80 parts of the compound represented by the formula (8) and 20 parts of the exemplary compound (1-1).

Example 7

An electrophotographic photosensitive member was produced in the same manner as in Example 1 except that the protective layer coating solution was prepared using a protective layer coating solution that contained 60 parts of the compound represented by the formula (8) and 40 parts of the exemplary compound (1-1).

Example 8

An electrophotographic photosensitive member was produced in the same manner as in Example 1 except that the protective layer coating solution was prepared using the exemplary compound (1-15) instead of the exemplary compound (1-1) and a compound represented by the following formula (9) instead of the compound represented by the formula (8).

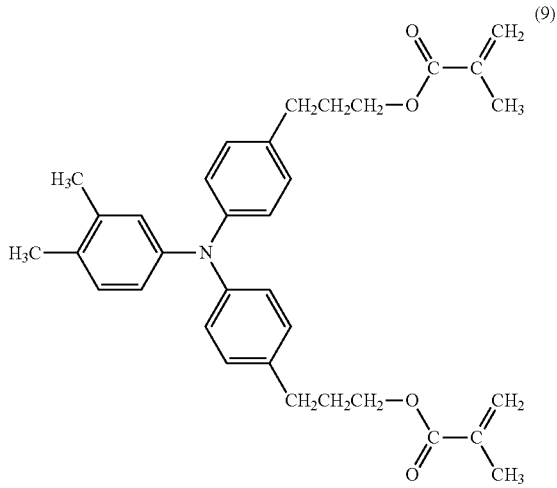

(9)

Example 9

An electrophotographic photosensitive member was produced in the same manner as in Example 5 except that the protective layer coating solution was prepared using the exemplary compound (2-1) instead of the exemplary compound (1-1).

Example 10

An electrophotographic photosensitive member was produced in the same manner as in Example 6 except that the protective layer coating solution was prepared using the exemplary compound (2-1) instead of the exemplary compound (1-1).

Example 11

An electrophotographic photosensitive member was produced in the same manner as in Example 7 except that the protective layer coating solution was prepared using the exemplary compound (2-1) instead of the exemplary compound (1-1).

Example 12

An electrophotographic photosensitive member was produced in the same manner as in Example 11 except that the protective layer coating solution was prepared using the exemplary compound (2-4) instead of the exemplary compound (1-1).

Example 13

An electrophotographic photosensitive member was produced in the same manner as in Example 12 except that the protective layer coating solution was prepared using a compound represented by the formula (9) instead of the compound represented by the formula (8).

Example 14

An electrophotographic photosensitive member was produced in the same manner as in Example 1 except that the protective layer coating solution was prepared by dissolving 45 parts of trimethylolpropane triacrylate (trade name: TMPTA, manufactured by Daicel-Cytec Co., Ltd.) (a compound having an acryloyl group as a polymerizable functional group and no charge transporting structure), 45 parts of a compound represented by the following formula (10), and 10 parts of the exemplary compound (1-1) in 25 parts of n-propanol and adding 25 parts of 1,1,2,2,3,3,4-heptafluorocyclopentane (trade name: ZEORORA H, manufactured by Zeon Corp.) to the solution.

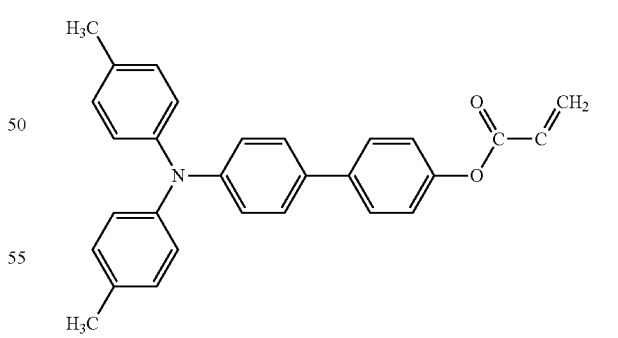

(10)

Example 15

An electrophotographic photosensitive member was produced in the same manner as in Example 14 except that the protective layer coating solution was prepared using the exemplary compound (2-1) instead of the exemplary compound (1-1).

Comparative Example 1

An electrophotographic photosensitive member was produced in the same manner as in Example 1 except that the protective layer coating solution was prepared without using the exemplary compound (1-1).

Comparative Example 2

An electrophotographic photosensitive member was produced in the same manner as in Example 1 except that the protective layer coating solution was prepared using a compound represented by the following formula (11) instead of the exemplary compound (1-1).

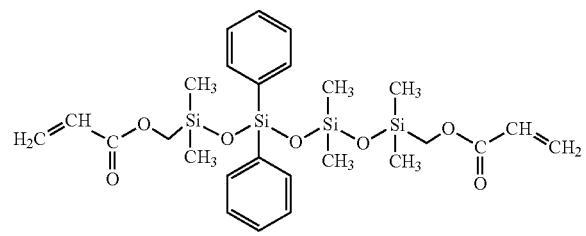

(11)

Comparative Example 3

An electrophotographic photosensitive member was produced in the same manner as in Example 1 except that the protective layer coating solution was prepared using a compound represented by the following formula (12) instead of the exemplary compound (1-1).

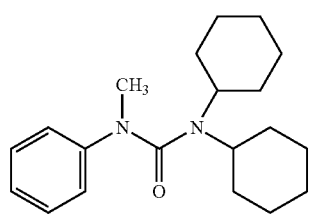

(12)

Comparative Example 4

An electrophotographic photosensitive member was produced in the same manner as in Example 1 except that the protective layer coating solution was prepared using a compound represented by the following formula (13) instead of the exemplary compound (1-1).

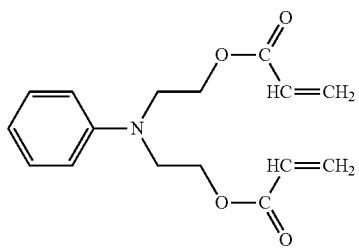

(13)

Comparative Example 5

An electrophotographic photosensitive member was produced in the same manner as in Example 14 except that the protective layer coating solution was prepared without using the exemplary compound (1-1).

Evaluation Method

The electrophotographic photosensitive members according to Examples 1 to 15 and Comparative Examples 1 to 5 were evaluated in the following manner. The electric potential stability of the electrophotographic photosensitive members was evaluated with respect to the variation in light area potential. Image deletion was evaluated with respect to image quality after repeated use of an electrophotographic photosensitive member.

Variation in Light Area Potential

An electrophotographic copying machine GP-405 (manufactured by CANON KABUSHIKI KAISHA) was used after modified such that a corona charger could be connected to an external power supply. The GP-405 was further modified such that the corona charger could be attached to a drum cartridge. A charger for an electrophotographic copying machine GP-55 (manufactured by CANON KABUSHIKI KAISHA) was used as the corona charger. The electrophotographic photosensitive member was attached to the drum cartridge, which was attached to the modified GP-405. The electric potential characteristics and image quality were evaluated as described below. A heater (drum heater (cassette heater)) for the electrophotographic photosensitive member was in the OFF position during the evaluation.

The surface potential of the electrophotographic photosensitive member was measured by removing a developing unit from the main body of the electrophotographic copying machine and fixing a potential measuring probe (model 6000B-8, manufactured by Trek Japan) at a position of development. A transferring unit was not in contact with the electrophotographic photosensitive member, and a paper sheet was not fed while measuring the surface potential.

The charger was connected to an external power supply. The power supply was controlled with a high-voltage supply controller (Model 610C, manufactured by Trek Inc.) such that the discharge current was 500 μA. The constant-current control scorotron grid applied voltage and light exposure conditions were controlled such that the electrophotographic photosensitive member had an initial dark area potential (Vd) of −650 (V) and an initial light area potential (Vl) of −200 (V).

The electrophotographic photosensitive member was installed in the copying machine. An image having an image ratio of 5% was printed on 1000 pieces of A4-size portrait paper at a temperature of 30° C. and a humidity of 80% RH. After that, the light area potential (Vl) was measured, and the potential variation ΔVl relative to the initial light area potential was calculated. Table 1 shows the results.

Image Quality after Repeated Use of Electrophotographic Photosensitive Member

After the evaluation of potential variation, the electrophotographic photosensitive member was again installed in the copying machine. After an image having an image ratio of 5% was printed on 9000 pieces of A4-size portrait paper (10,000 in total), the supply of electricity to the copying machine was stopped, and the copying machine was suspended for 72 hours. After 72 hours, electricity was again supplied to the copying machine. A lattice image (4 lines, 40 spaces) and a character image (E character image) consisting of letter E's of the alphabet (font: Times, 6-point) were printed on A4-size portrait paper.

Likewise, after printing of an additional 40,000 (50,000 in total) and 50,000 (100,000 in total) pieces of paper, the supply of electricity to the copying machine was stopped, and the copying machine was suspended for 72 hours. In each case, electricity was again supplied to the copying machine after 72 hours, and the lattice image and the E character image were printed on A4-size portrait paper.

The printed images were rated in accordance with the following criteria. Levels 5, 4, and 3 have the advantages of the present invention, and level 5 is excellent. Levels 1 and 2 lack the advantages of the present invention. Table 1 shows the results.

Level 5: Both the lattice image and the E character image have no image defect.

Level 4: The lattice image is partly blurred, but the E character image has no image defect.

Level 3: The lattice image is partly blurred, and the E character image is partly thin.

Level 2: The lattice image is partly lost, and the E character image is thin over the entire surface.

Level 1: The lattice image is lost over the entire surface, and the E character image is thin over the entire surface.

TABLE 1

| | Paper feed durability evaluation | | | |
|---|---|---|---|---|
| | Variation in light area potential after printing on 1000 pieces of paper (V) | Image level after printing on 10000 pieces of paper | Image level after printing on 50000 pieces of paper | Image level after printing on 100000 pieces of paper |
| Example 1 | 25 | 5 | 5 | 3 |
| Example 2 | 25 | 5 | 5 | 4 |
| Example 3 | 25 | 5 | 5 | 3 |
| Example 4 | 25 | 5 | 5 | 4 |
| Example 5 | 25 | 5 | 4 | 3 |
| Example 6 | 25 | 5 | 5 | 3 |
| Example 7 | 30 | 5 | 5 | 4 |
| Example 8 | 25 | 5 | 5 | 3 |
| Example 9 | 25 | 5 | 4 | 4 |
| Example 10 | 25 | 5 | 5 | 4 |
| Example 11 | 30 | 5 | 5 | 4 |
| Example 12 | 25 | 5 | 5 | 4 |
| Example 13 | 20 | 5 | 5 | 4 |
| Example 14 | 50 | 5 | 4 | 3 |
| Example 15 | 50 | 5 | 5 | 4 |
| Comparative example 1 | 25 | 2 | 1 | 1 |
| Comparative example 2 | 55 | 3 | 1 | 1 |
| Comparative example 3 | 80 | 2 | 2 | 1 |
| Comparative example 4 | 90 | 2 | 2 | 1 |
| Comparative example 5 | 60 | 2 | 1 | 1 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-115863 filed May 24, 2011 and No. 2012-100964 filed Apr. 26, 2012, which are hereby incorporated by reference herein in their entirety.

What is claimed is:

1. An electrophotographic photosensitive member, comprising:
a conductive support,
a photosensitive layer provided on the support,
wherein the electrophotographic photosensitive member comprises a surface layer comprising a polymer obtained by the polymerization of a composition comprising:
a charge transporting substance with at least one chain-polymerizable functional group, and
a urea compound,
wherein the urea compound is at least one compound selected from the group consisting of a compound represented by the following formula (1) and a compound represented by the following formula (2); and

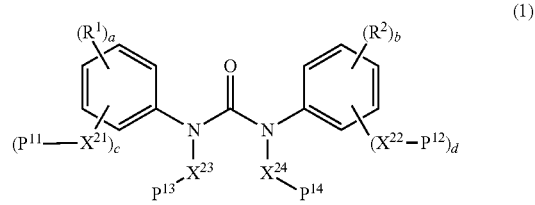

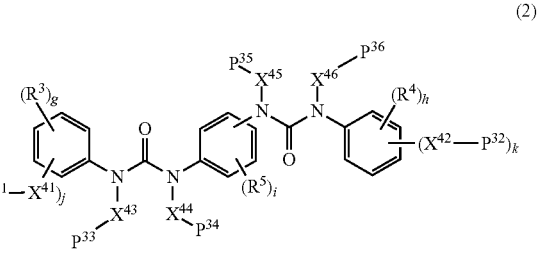

wherein, in the formulas (1) and (2),
$R^1$ to $R^5$ each independently represents an unsubstituted or substituted alkyl group, an unsubstituted or substituted alkoxyl group, a dialkylamino group, or a halogen atom,
$X^{21}$ to $X^{24}$, and $X^{41}$ to $X^{46}$ each independently represents an alkylene group, $p^{11}$ to $p^{14}$, and $P^{31}$ to $P^{36}$ each independently represents a hydrogen atom, an acryloyloxy group or a methacryloyloxy group,
at least one of the $P^{11}$ to $P^{14}$ is an acryloyloxy group or a methacryloyloxy group, at least one of the $P^{31}$ to $P^{36}$ is an acryloyloxy group or a methacryloyloxy group,
a, b, g, and h each independently represents an integer number selected from 0 to 5,
i represents an integer number selected from 0 to 4, and
c, d, j, and k each independently represents 0 or 1,
with the proviso that the urea compound represented by the formula (1) and the urea compound represented by the formula (2) have acryloyloxy group or a methacryloyloxy group respectively.

2. An electrophotographic photosensitive member according to claim 1,
wherein, in the formulas (1) and (2),
$R^1$ to $R^5$ each independently represents an alkyl group, an alkoxy-substituted alkyl group, a halogen-substituted alkyl group, an alkoxy group, an alkoxy-substituted alkoxy group, or a halogen-substituted alkoxy group.

3. An electrophotographic photosensitive member according to claim 1,
wherein, in the formulas (1) and (2), a, b, g, and h are 0.

4. An electrophotographic photosensitive member according to claim 1,
wherein, in the formulas (1) and (2),
at least one of the $X^{21}$ to $X^{24}$ is an ethylene group or a n-propylene group, and
at least one of the $X^{41}$ to $X^{46}$ is an ethylene group or a n-propylene group.

5. An electrophotographic photosensitive member according to claim 1,
wherein, in the formulas (1) and (2),
c, d, j, and k are 0.

6. An electrophotographic photosensitive member according to claim 1,
the chain-polymerizable functional group of the charge transporting substance comprises an acryloyloxy group or a methacryloyloxy group.

7. An electrophotographic photosensitive member according to claim 1,
the charge transporting substance comprises two or more chain-polymerizable functional groups in the same molecular.

8. A process cartridge detachably attachable to a main body of an electrophotographic apparatus, wherein the process cartridge integrally supports:
the electrophotographic photosensitive member according to claim 1, and
at least one device selected from the group consisting of a charging device, a developing device, a transferring device, and a cleaning device.

9. An electrophotographic apparatus comprising:
the electrophotographic photosensitive member according to claim 1;
a charging device;
an exposure device;
a developing device; and
a transferring device.

10. A method of producing the electrophotographic photosensitive member according to claim 1,
wherein the method comprises the following steps of:
forming a coat for the surface layer by the use of a surface-layer coating solution comprising the charge transporting substance and the urea compound, and
forming the surface layer by the polymerization of the charge transporting substance and the urea compound in the coat.

11. A method of producing the electrophotographic photosensitive member according to claim 10,
wherein the polymerization of the charge transporting substance and the urea compound is effected by sending electron ray toward the coat.

* * * * *